United States Patent
Xiao

(10) Patent No.: US 7,060,456 B2
(45) Date of Patent: Jun. 13, 2006

(54) REGULATION OF HUMAN PROTEIN PHOSPHATASE IIC-LIKE ENZYME

(75) Inventor: Yonghong Xiao, Cambridge, MA (US)

(73) Assignee: Bayer HealthCare AG, Leverkusen (DE)

( * ) Notice: Subject to any disclaimer, the term of this patent is extended or adjusted under 35 U.S.C. 154(b) by 515 days.

(21) Appl. No.: 10/362,772

(22) PCT Filed: Aug. 20, 2001

(86) PCT No.: PCT/EP01/09558

§ 371 (c)(1),
(2), (4) Date: Feb. 26, 2003

(87) PCT Pub. No.: WO92/18565

PCT Pub. Date: Mar. 7, 2002

(65) Prior Publication Data

US 2005/0271666 A1    Dec. 8, 2005

Related U.S. Application Data

(60) Provisional application No. 60/228,758, filed on Aug. 30, 2000, provisional application No. 60/280,115, filed on Apr. 2, 2001.

(51) Int. Cl.
*C12Q 1/44* (2006.01)
*C12N 9/16* (2006.01)

(52) U.S. Cl. ........................................ 435/19; 435/196

(58) Field of Classification Search .................. 435/19, 435/196
See application file for complete search history.

(56) References Cited

FOREIGN PATENT DOCUMENTS

| WO | WO 99 38972 | 8/1999 |
|---|---|---|
| WO | WO 99 58675 | 11/1999 |
| WO | WO 02 18424 | 3/2002 |

OTHER PUBLICATIONS

Kashiwaba et al (2003) FEBS Letters, vol. 538, pp. 197-202.*
Database EMBL "Online" Dec. 16, 1999 Database accession No. AL133644 (XP002207991).
Database EMBL "Online" May 1, 2000 Database accession No. Q9UF84 (XP002208006).
Database EMBL "Online" May 19, 2000 Database accession No. AAA02311 (XP002207992).
Database EMBL "Online" Oct. 12, 1999 Database accession No. AAZ12841 (XP002207993).
Database EMBL "Online" Oct. 21, 1999 Database accession No. AW117553 (XP002208045).
Database EMBL "Online" Jun. 19, 1998 Database accession No. AI024671 (XP002208046).
Database EMBL "Online" Oct. 6, 1998 Database accession No. AI167220 (XP002208047).
Database EMBL "Online" Aug. 3, 2001 Database accession No. BC011803 (XP002207994).
Database EMBL "Online" Feb. 8, 2001 Database accession No. AK009235 (XP002207995).
Database EMBL "Online" Jun. 6, 2002 Database accession No. AX400071 (XP002208000).
Barford, D: "Molecular mechanisms of the protein serine/threonine phosphatases", TIBS Trends in Biochemical Sciences Elsevier Publication, vol. 21, No. 11, Nov. 1, 1996, pp. 407-412 , XP004071015.
Price, N.E. and Mumby, M.C.: "Brain protein serine/threonine phosphates", Current Opinion in Neurobiology, vol. 9, 1999, pp. 336-342, XP002207990.
Tong, Y et al.: "Cloning and characterization of a Novel Mammalian PP2C Isozyme", The Journal of Biological Chemistry, vol. 273, No. 52, Dec. 25, 1998, pp. 35282-35290.
Kusuda, K. et al.: Mutational analysis of the domain structure of mouse protein phosphatase 2Cβ, Biochem J., (1998) 332, pp. 243-250.

* cited by examiner

Primary Examiner—Elizabeth Slobodyansky
(74) Attorney, Agent, or Firm—Banner & Witcoff, Ltd.

(57) ABSTRACT

Reagents which regulate human protein phosphatase IIC-like enzyme-like enzyme activity and reagents which bind to human protein phosphatase IIC-like enzyme-like enzyme gene products can be used, inter alia, to treat disorders associated with an increase in apoptosis, including AIDS and other infectious or genetic immunodeficiencies, neurodegenerative diseases, myelodysplasia, ischemic injuries, toxin-induced diseases, wasting diseases, viral infections, and osteoporosis. Regulation of human protein phosphatase IIC-like enzyme-like enzyme also can be used to treat disorders associated with a decrease in apoptosis, including cancer, diabetes, CNS disorders, cardiovascular disorders, chronic obstructive pulmonary diseases, and inflammatory disorders also can be treated.

3 Claims, 14 Drawing Sheets

Fig. 1 atggcctcacggctcctgcatcgccatatccgagagcagctaaaggacctgaa
ggaagtgagccacgagagcctggtagtgggggccattgagaatgccttccagc
tcatggatgagcagatggcccgggagcggcgtggccaccaagtggagggggc
tgctgtgcactggttgtgatctacctgctaggcaaggtgtacgtggccaatgc
aggcgatagcagggccatcattgtccggaatggtgaaatcattccaatgtccc
gggagtttaccccggagactgagcgccagcgtcttcagctgcttggcttcctg
aaaccagagctgctaggcagtgaattcacccaccttgagttccccgcagagt
tctgcccaaggagctggggcagaggatgttgtaccgggaccagaacatgaccg
gctgggcctacaaaaagatcgagctggaggatctcaggtttcctctggtctgt
ggggagggcaaaaaggctcgggtgatggccaccattggggtgacccgaggctt
gggagaccacagccttaaggtctgcagttccaccctgcccatcaagcctttc
tctcctgcttccctgaggtacgagtgtatgacctgacacaatatgagcactgc
ccagatgatgtgctagtcctgggaacagatggcctgtgggatgtcactactga
ctgtgaggtagctgccactgtggacagggtgctgtcggcctatgagcctaatg
accacagcaggtatacagctctggcccaagctctggtcctggggccggggt
acccccgagaccgtggctggcgtctcccaacaacaagctgggttccgggga
tgacatctctgtcttcgtcatcccctgggagggccaggcagttactcctga

Fig. 2

| MASRLLHRHI | REQLKDLKEV | SHESLVVGAI | ENAFQLMDEQ |
| MARERRGHQV | EGGCCALVVI | YLLGKVYVAN | AGDSRAIIVR |
| NGEIIPMSRE | FTPETERQRL | QLLGFLKPEL | LGSEFTHLEF |
| PRRVLPKELG | QRMLYRDQNM | TGWAYKKIEL | EDLRFPLVCG |
| EGKKARVMAT | IGVTRGLGDH | SLKVCSSTLP | IKPFLSCFPE |
| VRVYDLTQYE | HCPDDVLVLG | TDGLWDVTTD | CEVAATVDRV |
| LSAYEPNDHS | RYTALAQALV | LGARGTPRDR | GWRLPNNKLG |
| SGDDISVFVI | PLGGPGSYS | | |

Fig. 3

```
gggtgcgctcggccgtggcgcacctggtgagctccgggggcgctccgcctccg
cgccccaaatccccggacctgcccaacgccgcctcggcgccgcccgccgccgc
tccagaagcgcccaggagccctcccgcgaaggctgggagcgggagcgcgacgc
ccgcgaaggctgttgaggctcgagcgagcttctccagaccgacctttctgcag
ctgagccccggggggctgcgacgcgccgatgaccacgcgggccgggctgtgca
aagccccccggacacgggccgccgcctgccctggagcacaggctacgccgagt
gagcgcccctggggcacccaaaccaggatggggctcccacccctctccccag
ctccgcatccccggcgctaggacgcgttccccacgccgcgtccgggccaggag
ctccctttccgtggacctttgctatcctctggtcttcgggccgcaccccctc
ccaacccatttccagtgggggcagcctgtgtcaccttcttcacgtccttcc
cgctcattgactgccctcgcccacgccgcctcaggaccctgttctgcccaga
gcccggagggcggagagcccggcgaaggatgagttggccagttcccgtcgcg
gcccggcagcttaaaggctaagggaaaaggggtttcacgaaggagcggggttc
tttttaataggggacatagcggttgggaagactcgctcacccgcttcccggct
ccagcgcccagttccctgtcctcttaccgtagttcccctcccctccacac
ccagaaatagccgcgacaccaggaggccgccagcttccccaggagcggggag
ggggacgcccggggtagaggagggtcccatttagatgcccttcagcctgccaa
ctcgtgctggcctggcaaagaagcggaccccctgcccggagcggccggctggc
ccccgggctgtgtgtatttaaatgcatctgccgggaacgcagagcaccgagg
gagatggggcgctcagttcgctgaggaaggtggctggtggccatggaccca
ccaccacctcccttagcctcctgtgtgggaggagtttatgggtatgtggctcc
tgcccagtccaggtgggctttcacttctactctatttcagttcctctttcccg
atctgggctggagagcttcctcattgttaaggcagcagaaactttcgctggat
ggttttaggataaggggtcatcaatgctggcaagagtcggcacaatgaggacc
aggcttgctgtgaagtggtgtatgtggaaggtcggaggagtgttacaggagta
cctagggagcctagccgaggccagggactctgcttctactactggggcctatt
tgatgggcatgcagggggcggagctgctgaaatggcctcacggctcctgcatc
gccatatccgagagcagctaaaggacctgaaggaagtgagccacgagagcctg
gtagtgggggccattgagaatgccttccagctcatggatgagcagatggcccg
ggagcggcgtggccaccaagtggaggggggctgctgtgcactggttgtgatct
acctgctaggcaaggtgtacgtggccaatgcaggcgatagcagggccatcatt
gtccggaatggtgaaatcattccaatgtcccgggagtttaccccggagactga
gcgccagcgtcttcagctgcttggcttcctgaaaccagagctgctaggcagtg
aattcacccaccttgagttccccgcagagttctgcccaaggagctggggcag
aggatgttgtaccgggaccagaacatgaccggctgggcctacaaaaagatcga
gctggaggatctcaggtttcctctggtctgtggggagggcaaaaaggctcggg
tgatggccaccattggggtgacccgaggcttgggagaccacagccttaaggtc
tgcagttccaccctgcccatcaagccctttctcctgcttccctgaggtacg
agtgtatgacctgacacaatatgagcactgcccagatgatgtgctagtcctgg
gaacagatggcctgtgggatgtcactactgactgtgaggtagctgccactgtg
gacagggtgctgtcggcctatgagcctaatgaccacagcaggtatacagctct
ggcccaagctctggtcctgggggcccggggtacccccgagaccgtggctggc
gtctccccaacaacaagctgggttccggggatgacatctctgtcttcgtcatc
cccctgggagggccaggcagttactcctgaggggctgaacaccatccctccca
ctagcctctccatacttactcctctcacagcccaaattctgaagttgtctccc
tgacccttctttagtggcaacttaactgaagaagggatgtccgctatatccaa
aattacagctattggcaaataaacgagatggataaaaaaaaaaaaaaaaaaa
aaaaaaaaaaaaaaaaaaaaaaaaa
```
CDS = 1410..2309

Fig. 4

| | | | |
|---|---|---|---|
| MAGICCGVVG | ETEPAAPVDS | TSRASLRRRL | DLLPSIKIVA |
| DSAVAPPLEN | CRKRQKRETV | VLSTLPGNLD | LDSNVRSENK |
| KARSAVTNSN | SVTEAESFFS | DVPKIGTTSV | CGRRRDMEDA |
| VSIHPSFLQR | NSENHHFYGV | FDGHGCSHVA | EKCRERLHDI |
| VKKEVEVMAS | DEWTETMVKS | FQKMDKEVSQ | RECNLVVNGA |
| TRSMKNSCRC | ELQSPQCDAV | GSTAVVSVVT | PEKIIVSNCG |
| DSRAVLCRNG | VAIPLSVDHK | PDRPDELIRI | QQAGGRVIYW |
| DGARVLGVLA | MSRAIGDNYL | KPYVIPDPEV | TVTDRTDEDE |
| CLILASDGLW | DVVPNETACG | VARMCLRGAG | AGDDSDAAHN |
| ACSDAALLLT | KLALARQSSD | NVSVVVVDLR | KRRNNQASS |

Fig. 5

TTTTTATCCATCTCGTTTATTTGCCAATAGCTGTAATTTTGGATATAGCGGAC
ATCCCTTCTTCAGTTAAGTTGCCACTAAAGAAGGGTCAGGGAGACAACTTCAG
AATTTGGGCTGTGAGAGGAGTAAGTATGGAGAGGCTAGTGGGAGGGATGGTGT
TCAGCCCCTCAGGAGTAACTGCCTGGCCCTCCCAGGGGGATGACGAAGACAGA
GATGTCATTCCCGGAACCCAGCTTGTTGTTGGGGAGACACCAGCCACGGTCTC
GGGGGGTACCCCGGGCCCCCAGGACCAGAGCTTGGGCCAGAGCTGTATACCTG
CTGTGGTCATTAGGCTCATAGGCCGACAGCACCCTGTCCACAGTGGCAGCTAC
CTCACAGTCAGTAGTGACATCCCACAGGCCATCTGTTCCCAAGACTAGCACAT
CATCTGGGCAGTGCTCATATTGTGTCAGGTCATACACTCNTACCTCANGGAAG
CAGGAAAAAAGGGCTTGATGGG

Fig. 6

```
TTTTTTTATCCATCTCGTTTATTTGCCAATAGCTGTAATTTTGGATATAGCGG
ACATCCCTTCTTCAGTTAAGTTGCCACTAAAGAAGGGTCAGGGAGACAACTTC
AGAATTTGGGCTGTGAGAGGAGTAAGTATGGAGAGGCTAGTGGGAGGGATGGT
GTTCAGCCCCTCAGGAGTAACTGCCTGGCCCTCCCAGGGGGNATGACGAAGAC
AGAGATGTCATCCCCGGAACCCAGCTTGTTGTTGGGGAGACGCCAGCCACGGT
CTCGGGGGGTACTCGGGCCCCAGGACCAGAGCTTGGGCCAGAGCTGTATACC
TGCTGTGGTCATTAGGCTCATAGGCCGACAGCACCCTGTCCACAGTGGCAGCT
ACCTCACAGTCAGTAGTGACATCCCACAGGCCATCTGTTCCCAGGACTAGCAC
ATCATCTGGGCAGTGCTCATATTGTGTCAGGTCATACACTCGTACCTCA
```

Fig. 7

```
TCCATCTCGTTTATTTGCCAATAGCTGTAATTTTGGATATAGCGGACATCCCT
TCTTCAGTTAAGTTGCCACTAAAGAAGGGTCAGGGAGACAACTTCAGAATTTG
GGCTGTGAGAGGAGTAAGTATGGAGAGGCTAGTGGGAGGGATGGTGTTCAGCC
CCTCAGGAGTAACTGCCTGGCCCTCCCAGGGGGATGACGAAGACAGAGATGTC
ATCCCCGGAACCCAGCTTGTTGTTGGGGAGACGCCAGCCACGGTCTCGGGGGG
TACCCCGGGCCCCCAGGACCAGAGCTTGGGCCAGAGCTGTATACCTGCTGTGG
TCATTAGGCTCATAGGCCGACAGCACCCTGTCCACAGTGGCAGCTACCTCACA
GTCAGTAGTGACATCCCACAGGCCATCTGTTCCCAGGACTAGCACATCATCTG
GGCAGTGCTCATATTGTGTC
```

Fig. 8

TTTCCTTTATCCATCTCGTTTATTTGCCAATAGCTGTAATTTTGGATATAGCG
GACATCCCTTCTTCAGTTAAGTTGCCACTAAAGAAGGGTCAGGGAGACAACTT
CAGAATTTGGGCTGTGAGAGGAGTAAGTATGGAGAGGCTAGTGGGAGGGATGG
TGTTCAGCCCCTCAGGAGTAACTGCCTGGCCCTCCCAGGGGGATGACGAAGAC
AGAGATGTCATCCCCGGAACCCAGCTTGTTGTTGGGGAGACGCCAGCCACGGT
CTCGGGGGGTACCCCGGGCCCCAGGACCAGAGCTTGGGCCAGAGCTGTATAC
CTGCTGTGGTCATTAGGCTCATAGGCCGACAGCACCCTGTCCACAGTGGCAGC
TACCTCACAGTCAGTAGTGACATCCCACAGGCCATCTGTTCCCAGGACTAGCA
CATC

Fig. 9

```
TTTCCTTTATCCATCTCGTTTATTTGCCAATAGCTGTAATTTTGGATATAGCG
GACATCCCTTCTTCAGTTAAGTTGCCACTAAAGAAGGGTCAGGGAGACAACTT
CAGAATTTGGGCTGTGAGAGGAGTAAGTATGGAGAGGCTAGTGGGAGGGATGG
TGTTCAGCCCCTCAGGAGTAACTGCCTGGCCCTCCCAGGGGGATGACGAAGAC
AGAGATGTCATCCCCGGAACCCAGCTTGTTGTTGGGGAGACGCCAGCCACGGT
CTCTGGGGGTACCCCGGGCCCCAGGACCAGAGCTTGGGCCAGAGCTGTATAC
CTGCTGTGGTCATTAGGCTCATAGGCCGACAGCACCCTGTCCACAGTGGCAGC
TACCTCACAGTCAGTAGTGACATCCACAGGCCATCTGTTCCCAGGACTAGCA
CATC
```

Fig. 10

```
TTTTATCCATCTCGTTTATTTGCCAATAGCTGTAATTTTGGATATAGCGGACA
TCCCTTCTTCAGTTAAGTTGCCACTAAAGAAGGGTCAGGGAGACAACTTCAGA
ATTTGGGCTGTGAGAGGAGTAAGTATGGAGAGGCTAGTGGGAGGGATGGTGTT
CAGCCCCTCAGGAGTAACTGCCTGGCCCTCCCAGGGGGATGACGAAGACAGAG
ATGTCATCCCCGGAACCCAGCTTGTTGTTGGGGAGACGCCAGCCACGGTCTCT
GTGGGTACCCCGGGCCCCAGGACCAGAGCTTGGGCCAGAGCTGTATACCTGC
TGTGGACATTAGGCTCATAGGCCGACAGCACCCTGTCCACAGTGGCAGCTACC
TCACAGTCAGTAGTGACATCCACAGGCCATCTGTTCCCAGGACTAGCACATC
```

Fig. 11

```
ATGATCCATTCGCGCAATCAGCCATTACCTGTGCTTCGGGAGTATCCGCGCGC
ATCCGTTGTTTAGTTTATTCTTCACTAAGGAATGGTCAAGGAGCACCACTGTC
GACTGTGCCCTGCGAGAGTGATGACGTATCCAGAGGATAGTGCGACGTATGCG
GCCAGTCCCTCAGGAGTAACTGCCTGGCCCTCCCAGGGGGATGACGAAGACAG
AGATGTCATCCCCGGAACCCAGCTTGTTGTTGGGGAGACGCCAGCCACGGTCT
CGGGGGGTACCCCGGGCCCCCAGGACCAGAGCTTGGGCCAGAGCTGTATACCT
GCTGTGGTCATTAGGCTCATAGGCCGACAGCACCCTGTCCACAGTGGCAGCTA
CCTCACAGTCAGTAGTGAC
```

Fig. 12

```
TTTATCCATCTCATTTATTTGCCAATAGCTGTAATTTTGGATATAGCGGACAT
CCCTTCTTCAGTTAAGTTGCCACTAAAGAAGGGTCAGGGAGACAACTTCAGAA
TTTGGGCTGTGAGAGGAGTAAGTATGGAGAGGCTAGTGGGAGGGATGGTGTTC
AGCCCCTCAGGAGTAACTGCCTGGCCCTCCCAGGGGGNATGACGAAGACAGAG
ATGTCATCCCCGGAACCCAGCTTGTTGTTGGGGAGACGCCAGCCACGGTCTCG
GGGGGTACCCGGGCCCCCAGGACCAGAGCTTGGGCCAGAGCTGTATACCTGCT
GTGGTCATTAGGCTCATAGGCCGACAGCACCCTGTCCACAGTGGCAGCTA
```

FIG. 13

BLASTP - alignment of 61 (SEQ ID NO:2) against swiss|P49598|P2C4_ARATH
This hit is scoring at : 2e-10 (expectation value) Alignment length
overlap) : 279 Identities : 25 % Scoring matrix : BLOSUM62 (used to
infer consensus pattern) Database searched : nrdb

```
Q:  18 KEVSHESLVVGAIENAFQLMDEQMARERRGHQVEG-GCCALVIYLLGKVYVANAGDSRA
       KEVS... : ...A : M..... E :: Q.:. G..A:V :.. K:.V:N.GDSRA
H: 186 KEVSQRECNL-VVNGATRSMKNSCRCELQSPQCDAVGSTAVVSVVTPEKIIVSNCGDSRA

IIVRNGEIIPMSREFTPETERQRLQLLGFLKPELLGSEFTHLEFPRRVLPKELGQRMLYR
       :::.RNG .IP:S ...P:. . ::: ::: :.:G R::Y
       VLCRNGVAIPLSVDHKPDRPDELIRI------------------QQAGGRVIYW

DQNMTGWAYKKIELEDLRFPLVCGEGKKARVMATIGVTRGLGDHSLKVCSSTLPIKPFLS
       D ARV:...::R.:GD: LK P::
       DG-----------------------ARVLGVLAMSRAIGDNYLK--------PYVI

CFPEVRVYDLTQYEHCPDDVLVLGTDGLWDVT---TDCEVAATVDRVLSAYEPNDHSRYT
       PEV.V D T. :.C L:L.:DGLWDV. T C VA... R .A :::D ..
       PDPEVTVTDRTDEDEC----LILASDGLWDVVPNETACGVARMCLRGAGAGDDSDAAHNA
                          BLOCKS PP2C region
       ALAQAIVLGARGTPRDRGWRLPNNKLGSGDDISVFVIPL 292
       . .AL:L . ...R. S.D::SV.V:. L
       CSDAALLLTKLALARQ------------SSDNVSVVVDL 389
```

FIG. 14

BLOCKS search result

| AC# | Description | Strength Score |
|---|---|---|
| BL01032H | 0 Protein phosphatase 2C proteins. | 1495 1234 |

AA# 213 DDvLVLGtDGLWD

FIG. 15

MMPFAM - alignment of 61 (SEQ ID NO:2) against pfam|hmm|PP2C
Protein phosphatase 2C
This hit is scoring at : 41.5; Expect = 8.5e-11
Scoring matrix : BLOSUM62 (used to infer consensus pattern)

```
Q:   1 MASRLLHRHIREQLKDLKEVSHES------LVVGAIENAFQL--MDEQMAR----ERR
       .A:.. :H:.::: :: E.     : .A:..:F  .DE:.: ...
H:  48 qaakyagkhlhktilaerksfpegdpwEmklsdledalkesfleadtdeelrsaeasaan ----GHQVEGGCCALVVIYLLGKVYVANAGDSRAIIVRNGEII----PMSR         89
           ..:.G..A:V.:.   .K:YVAN.GDSRA::.RNG.. I   .:: .
       kvltkedlssGsTAvvalirgnkLyVANvGDSRavLcrngnaikwavtLte         158
```

Protein phosphatase 2C
This hit is scoring at : 12.7; Expect = 0.013
Scoring matrix : BLOSUM62 (used to infer consensus pattern)

```
Q: 173 VTRGLGDHSLK---VCSSTL---------PikPFLSCFPEVR-VYDLTQYEhcpDDV
       V:R..GD..LK    ....           . .::: P:V.   DLT.   D:.
H: 192 vSRAfGDfelKpgsklgpeesleanyeyikspe..qlVtaePdvtsstdltpdk...DeF LVLGTDGLWDVTTDCEVAATVDRVLSA                                 243
       L:L..DGLWDV.:D EV. .V . LS
       liLAcDGLWDvvsdgevvdivrselsd                                 273
```

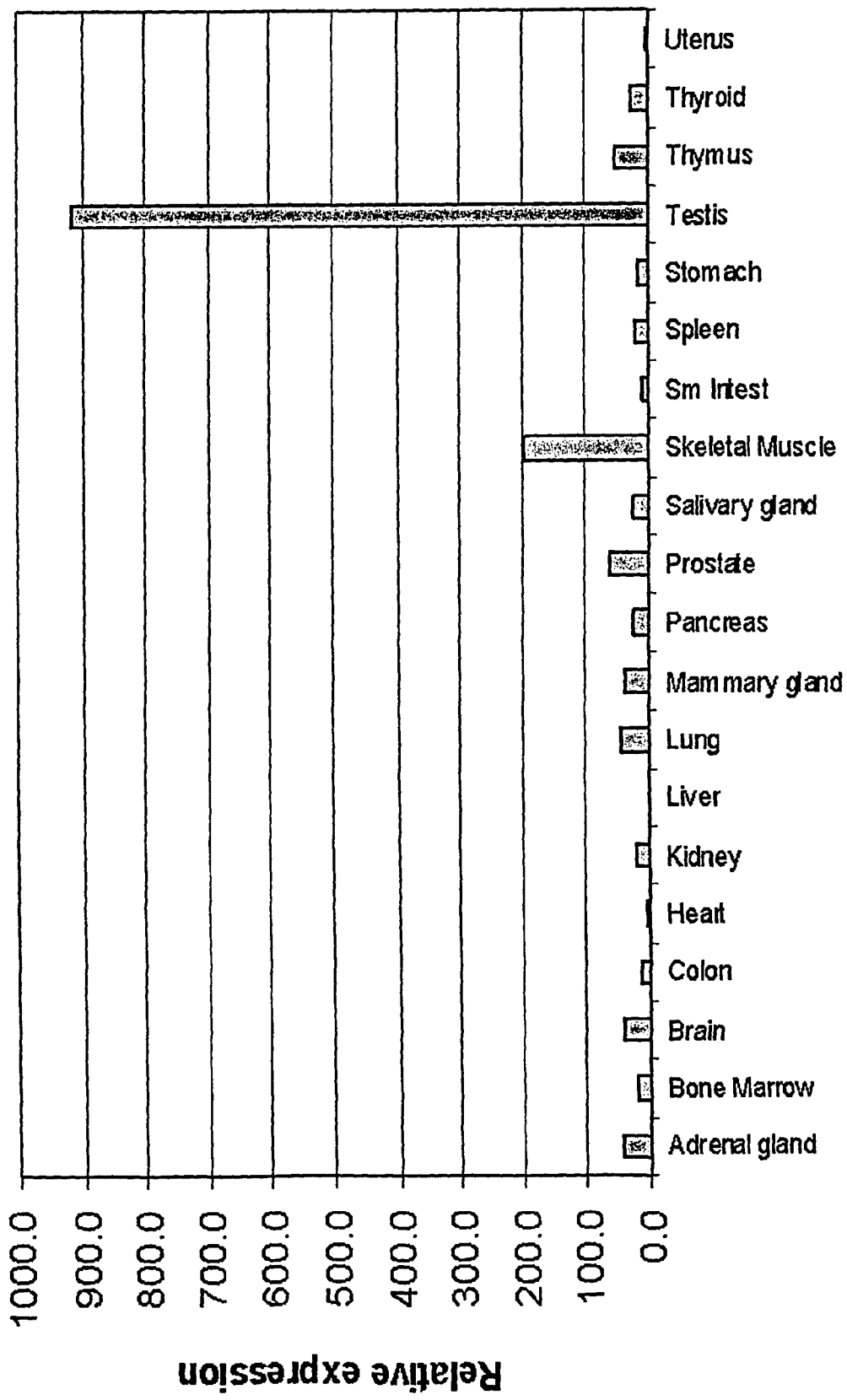
FIG. 16. Relative expression of protein phosphatase IIC-like enzyme in various human tissues.

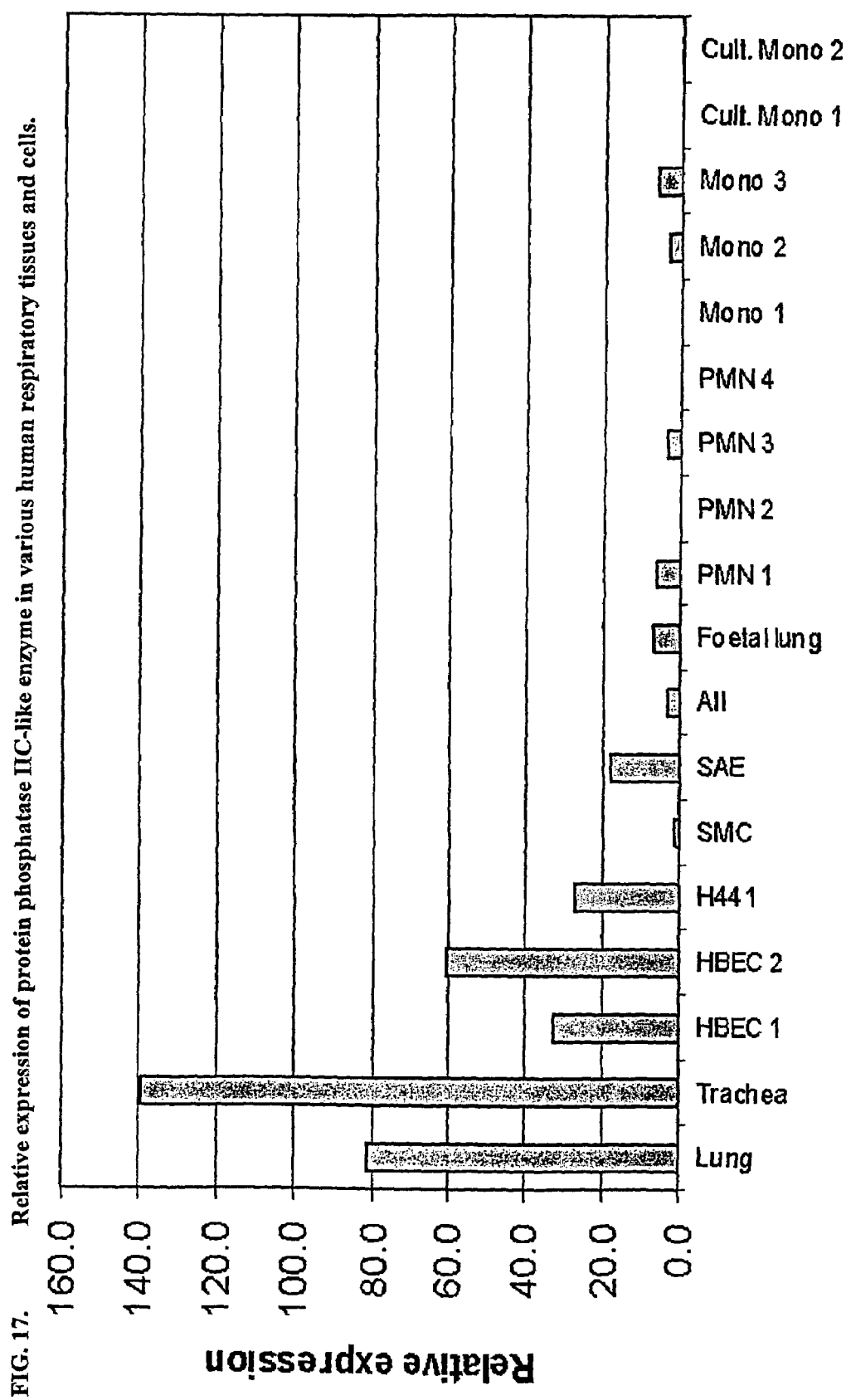
FIG. 17. Relative expression of protein phosphatase IIC-like enzyme in various human respiratory tissues and cells.

SEQUENCE LISTING

<160> NUMBER OF SEQ ID NOS: 12

<210> SEQ ID NO 1
<211> LENGTH: 900
<212> TYPE: DNA
<213> ORGANISM: Homo sapiens

<400> SEQUENCE: 1

```
atggcctcac ggctcctgca tcgccatatc cgagagcagc taaaggacct gaaggaagtg      60
agccacgaga gcctggtagt gggggccatt gagaatgcct tccagctcat ggatgagcag     120
atggcccggg agcggcgtgg ccaccaagtg gagggggggct gctgtgcact ggttgtgatc     180
tacctgctag gcaaggtgta cgtggccaat gcaggcgata gcagggccat cattgtccgg     240
aatggtgaaa tcattccaat gtcccgggag tttaccccgg agactgagcg ccagcgtctt     300
cagctgcttg gcttcctgaa accagagctg ctaggcagtg aattcacccca ccttgagttc     360
ccccgcagag ttctgcccaa ggagctgggg cagaggatgt tgtaccggga ccagaacatg     420
accggctggg cctacaaaaa gatcgagctg gaggatctca ggtttcctct ggtctgtggg     480
gagggcaaaa aggctcgggt gatggccacc attggggtga cccgaggctt gggagaccac     540
agccttaagg tctgcagttc caccctgccc atcaagccct ttctctcctg cttccctgag     600
gtacgagtgt atgacctgac acaatatgag cactgcccag atgatgtgct agtcctggga     660
acagatggcc tgtgggatgt cactactgac tgtgaggtag ctgccactgt ggacagggtg     720
ctgtcggcct atgagcctaa tgaccacagc aggtatacag ctctggccca agctctggtc     780
ctgggggccc gggtaccccc ccgagaccgt ggctggcgtc tccccaacaa caagctgggt     840
tccggggatg acatctctgt cttcgtcatc cccctgggag ggccaggcag ttactcctga     900
```

<210> SEQ ID NO 2
<211> LENGTH: 299
<212> TYPE: PRT
<213> ORGANISM: Homo sapiens

<400> SEQUENCE: 2

```
Met Ala Ser Arg Leu Leu His Arg His Ile Arg Glu Gln Leu Lys Asp
1               5                   10                  15

Leu Lys Glu Val Ser His Glu Ser Leu Val Val Gly Ala Ile Glu Asn
            20                  25                  30

Ala Phe Gln Leu Met Asp Glu Gln Met Ala Arg Glu Arg Arg Gly His
        35                  40                  45
```

```
Gln Val Glu Gly Gly Cys Cys Ala Leu Val Val Ile Tyr Leu Leu Gly
 50                  55                  60

Lys Val Tyr Val Ala Asn Ala Gly Asp Ser Arg Ala Ile Ile Val Arg
 65                  70                  75                  80

Asn Gly Glu Ile Ile Pro Met Ser Arg Glu Phe Thr Pro Glu Thr Glu
                 85                  90                  95

Arg Gln Arg Leu Gln Leu Leu Gly Phe Leu Lys Pro Glu Leu Leu Gly
            100                 105                 110

Ser Glu Phe Thr His Leu Glu Phe Pro Arg Arg Val Leu Pro Lys Glu
        115                 120                 125

Leu Gly Gln Arg Met Leu Tyr Arg Asp Gln Asn Met Thr Gly Trp Ala
130                 135                 140

Tyr Lys Lys Ile Glu Leu Glu Asp Leu Arg Phe Pro Leu Val Cys Gly
145                 150                 155                 160

Glu Gly Lys Lys Ala Arg Val Met Ala Thr Ile Gly Val Thr Arg Gly
                165                 170                 175

Leu Gly Asp His Ser Leu Lys Val Cys Ser Ser Thr Leu Pro Ile Lys
            180                 185                 190

Pro Phe Leu Ser Cys Phe Pro Glu Val Arg Val Tyr Asp Leu Thr Gln
        195                 200                 205

Tyr Glu His Cys Pro Asp Asp Val Leu Val Leu Gly Thr Asp Gly Leu
210                 215                 220

Trp Asp Val Thr Thr Asp Cys Glu Val Ala Ala Thr Val Asp Arg Val
225                 230                 235                 240

Leu Ser Ala Tyr Glu Pro Asn Asp His Ser Arg Tyr Thr Ala Leu Ala
                245                 250                 255

Gln Ala Leu Val Leu Gly Ala Arg Gly Thr Pro Arg Asp Arg Gly Trp
            260                 265                 270

Arg Leu Pro Asn Asn Lys Leu Gly Ser Gly Asp Asp Ile Ser Val Phe
        275                 280                 285

Val Ile Pro Leu Gly Gly Pro Gly Ser Tyr Ser
290                 295

<210> SEQ ID NO 3
<211> LENGTH: 2518
<212> TYPE: DNA
<213> ORGANISM: Homo sapiens
<220> FEATURE:
<221> NAME/KEY: gene
<222> LOCATION: (1410)..(2309)
<223> OTHER INFORMATION: CDS

<400> SEQUENCE: 3
gggtgcgctc ggccgtggcg cacctggtga gctccggggg cgctccgcct ccgcgcccca     60
aatccccgga cctgcccaac gccgcctcgg cgccgcccgc cgccgctcca gaagcgccca    120
ggagccctcc cgcgaaggct gggagcggga gcgacgcc cgcgaaggct gttgaggctc     180
gagcgagctt ctccagaccg acctttctgc agctgagccc cggggggctg cgacgcgccg    240
atgaccacgc gggccgggct gtgcaaagcc ccccggacac gggccgccgc ctgccctgga    300
gcacaggcta cgccgagtga gcgccccctg ggcacccaa accaggatgg ggctcccacc     360
cctctcccca gctccgcatc cccggcgcta ggacgcgttc ccacgccgc gtccgggcca     420 ggagctccct tttccgtgga cctttgctat cctctggtct tcggccgca ccccctccca     480 acccatttc cagtggggg cagcctgtgt caccttcttc acgtccttcc cgctcattga     540
ctgccctcgc ccacgccgcc tcaggaccct gttctgcccc agagcccgga gggcggagag    600
```

-continued

```
cccggcgaag gatgagttgg ccagttcccc gtcgcggccc ggcagcttaa aggctaaggg      660
aaaaggggtt tcacgaagga gcggggttct ttttaatagg ggacatagcg gttgggaaga     720
ctcgctcacc cgcttcccgg ctccagcgcc ccagttccct gtccctctta ccgtagttcc     780 cctcccccctc cacacccaga aatagcccgc gacaccagga ggccgccagc ttccccagga    840
gcggggaggg ggacgcccgg ggtagaggag ggtcccattt agatgcccct cagcctgcca     900
actcgtgctg gcctggcaaa gaagcggacc ccctgcccgg agcggccggc tggcccccgg     960
gctgtgtgta tttttaaatgc atctgccggg aacgcagagc accgagggag atggggggcgc  1020 tcagttcgct gaggaaggtg gctggtggcc catggaccca ccaccactc ccttagcctc      1080 ctgtgtggga ggagtttatg ggtatgtggc tcctgcccag tccaggtggg ctttcacttc    1140
tactctattt cagttcctct ttcccgatct gggctggaga gcttcctcat tgttaaggca    1200
gcagaaactt tcgctggatg gttttaggat aagggtcat caatgctggc aagagtcggc     1260
acaatgagga ccaggcttgc tgtgaagtgg tgtatgtgga aggtcggagg agtgttacag    1320
gagtacctag ggagcctagc cgaggccagg gactctgctt ctactactgg ggcctatttg    1380
atgggcatgc aggggggcgga gctgctgaaa tggcctcacg gctcctgcat cgccatatcc   1440
gagagcagct aaaggacctg aaggaagtga gccacgagag cctggtagtg ggggccattg    1500 agaatgccctt ccagctcatg gatgagcaga tggcccggga gcggcgtggc caccaagtgg   1560 agggggggctg ctgtgcactg gttgtgatct acctgctagg caaggtgtac gtggccaatg   1620
caggcgatag caggggccatc attgtccgga atggtgaaat cattccaatg tcccgggagt   1680 ttaccccggga gactgagcgc cagcgtcttc agctgcttgg cttcctgaaa ccagagctgc    1740
taggcagtga attcacccac cttgagttcc cccgcagagt tctgcccaag gagctggggc    1800
agaggatgtt gtaccgggac cagaacatga ccggctgggc ctacaaaaag atcgagctgg    1860
aggatctcag gtttcctctg gtctgtgggg agggcaaaaa ggctcgggtg atggccacca   1920 ttgggggtgac ccgaggcttg ggagaccaca gccttaaggt ctgcagttcc accctgccca   1980
tcaagccctt tctctcctgc ttccctgagg tacgagtgta tgacctgaca caatatgagc    2040
actgcccaga tgatgtgcta gtcctgggaa cagatggcct gtgggatgtc actactgact    2100
gtgaggtagc tgccactgtg gacagggtgc tgtcggccta tgagcctaat gaccacagca   2160
ggtatacagc tctggcccaa gctctggtcc tgggggcccg gggtaccccc cgagaccgtg    2220
gctggcgtct ccccaacaac aagctgggtt ccggggatga catctctgtc ttcgtcatcc    2280
ccctgggagg gccaggcagt tactcctgag gggctgaaca ccatccctcc cactagcctc   2340
tccatactta ctcctctcac agcccaaatt ctgaagttgt ctccctgacc cttctttagt    2400
ggcaacttaa ctgaagaagg gatgtccgct atatccaaaa ttacagctat ggcaaataa    2460 acgagatgga taaaaaaaaa aaaaaaaaa aaaaaaaaa aaaaaaaaa aaaaaaa         2518
```

<210> SEQ ID NO 4
<211> LENGTH: 399
<212> TYPE: PRT
<213> ORGANISM: Arabidopsis thaliana

<400> SEQUENCE: 4

```
Met Ala Gly Ile Cys Cys Gly Val Val Gly Glu Thr Glu Pro Ala Ala
 1               5                  10                  15

Pro Val Asp Ser Thr Ser Arg Ala Ser Leu Arg Arg Arg Leu Asp Leu
            20                  25                  30
```

```
Leu Pro Ser Ile Lys Ile Val Ala Asp Ser Ala Val Ala Pro Pro Leu
            35                  40                  45

Glu Asn Cys Arg Lys Arg Gln Lys Arg Glu Thr Val Val Leu Ser Thr
 50                  55                  60

Leu Pro Gly Asn Leu Asp Leu Asp Ser Asn Val Arg Ser Glu Asn Lys
 65                  70                  75                  80

Lys Ala Arg Ser Ala Val Thr Asn Ser Asn Ser Val Thr Glu Ala Glu
                 85                  90                  95

Ser Phe Phe Ser Asp Val Pro Lys Ile Gly Thr Thr Ser Val Cys Gly
                100                 105                 110

Arg Arg Arg Asp Met Glu Asp Ala Val Ser Ile His Pro Ser Phe Leu
            115                 120                 125

Gln Arg Asn Ser Glu Asn His His Phe Tyr Gly Val Phe Asp Gly His
    130                 135                 140

Gly Cys Ser His Val Ala Glu Lys Cys Arg Glu Arg Leu His Asp Ile
145                 150                 155                 160

Val Lys Lys Glu Val Glu Val Met Ala Ser Asp Glu Trp Thr Glu Thr
                165                 170                 175

Met Val Lys Ser Phe Gln Lys Met Asp Lys Glu Val Ser Gln Arg Glu
            180                 185                 190

Cys Asn Leu Val Val Asn Gly Ala Thr Arg Ser Met Lys Asn Ser Cys
    195                 200                 205

Arg Cys Glu Leu Gln Ser Pro Gln Cys Asp Ala Val Gly Ser Thr Ala
210                 215                 220

Val Val Ser Val Val Thr Pro Glu Lys Ile Ile Val Ser Asn Cys Gly
225                 230                 235                 240

Asp Ser Arg Ala Val Leu Cys Arg Asn Gly Val Ala Ile Pro Leu Ser
                245                 250                 255

Val Asp His Lys Pro Asp Arg Pro Asp Glu Leu Ile Arg Ile Gln Gln
            260                 265                 270

Ala Gly Gly Arg Val Ile Tyr Trp Asp Gly Ala Arg Val Leu Gly Val
    275                 280                 285

Leu Ala Met Ser Arg Ala Ile Gly Asp Asn Tyr Leu Lys Pro Tyr Val
290                 295                 300

Ile Pro Asp Pro Glu Val Thr Val Thr Asp Arg Thr Asp Glu Asp Glu
305                 310                 315                 320

Cys Leu Ile Leu Ala Ser Asp Gly Leu Trp Asp Val Val Pro Asn Glu
                325                 330                 335

Thr Ala Cys Gly Val Ala Arg Met Cys Leu Arg Gly Ala Gly Ala Gly
            340                 345                 350

Asp Asp Ser Asp Ala Ala His Asn Ala Cys Ser Asp Ala Ala Leu Leu
    355                 360                 365

Leu Thr Lys Leu Ala Leu Ala Arg Gln Ser Ser Asp Asn Val Ser Val
370                 375                 380

Val Val Val Asp Leu Arg Lys Arg Arg Asn Asn Gln Ala Ser Ser
385                 390                 395

<210> SEQ ID NO 5
<211> LENGTH: 500
<212> TYPE: DNA
<213> ORGANISM: Homo sapiens
<220> FEATURE:
<221> NAME/KEY: misc_feature
<222> LOCATION: (464)..(464)
<223> OTHER INFORMATION: n=a, c, g or t
```

```
<220> FEATURE:
<221> NAME/KEY: misc_feature
<222> LOCATION: (472)..(472)
<223> OTHER INFORMATION: n=a, c, g or t

<400> SEQUENCE: 5
tttttatcca tctcgtttat ttgccaatag ctgtaattt ggatatagcg gacatccctt     60
cttcagttaa gttgccacta agaagggtc agggagacaa cttcagaatt tgggctgtga    120
gaggagtaag tatggagagg ctagtgggag ggatggtgtt cagcccctca ggagtaactg    180
cctggccctc ccagggggat gacgaagaca gagatgtcat tcccggaacc cagcttgttg    240
ttggggagac accagccacg gtctcggggg gtaccccggg cccccaggac cagagcttgg    300
gccagagctg tatacctgct gtggtcatta ggctcatagg ccgacagcac cctgtccaca    360
gtggcagcta cctcacagtc agtagtgaca tcccacaggc catctgttcc caagactagc    420
acatcatctg ggcagtgctc atattgtgtc aggtcataca ctcntacctc anggaagcag    480
gaaaaaaagg gcttgatggg                                               500

<210> SEQ ID NO 6
<211> LENGTH: 473
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n=a, c, g or t

<400> SEQUENCE: 6 ttttttttatc catctcgttt atttgccaat agctgtaatt ttggatatag cggacatccc    60
ttcttcagtt aagttgccac taaagaaggg tcagggagac aacttcagaa tttgggctgt    120
gagaggagta agtatggaga ggctagtggg agggatggtg ttcagcccct caggagtaac    180
tgcctggccc tcccaggggg natgacgaag acagagatgt catccccgga acccagcttg    240
ttgttgggga gacgccagcc acggtctcgg ggggtactcg gccccccagg accagagctt    300
gggccagagc tgtatacctg ctgtggtcat taggctcata ggccgacagc acctgtcca    360 cagtggcagc tacctcacag tcagtagtga catcccacag gccatctgtt cccaggacta    420
gcacatcatc tgggcagtgc tcatattgtg tcaggtcata cactcgtacc tca          473

<210> SEQ ID NO 7
<211> LENGTH: 444
<212> TYPE: DNA
<213> ORGANISM: Homo sapiens

<400> SEQUENCE: 7
tccatctcgt ttatttgcca atagctgtaa ttttggatat agcggacatc ccttcttcag     60
ttaagttgcc actaaagaag ggtcaggag acaacttcag aatttgggct gtgagaggag    120
taagtatgga gaggctagtg ggagggatgg tgttcagccc ctcaggagta actgcctggc    180
cctcccaggg ggatgacgaa gacagagatg tcatccccgg aacccagctt gttgttgggg    240
agacgccagc cacggtctcg ggggtaccc cggcccccca ggaccagagc ttgggccaga    300
gctgtatacc tgctgtggtc attaggctca taggccgaca gcaccctgtc cacagtggca    360
gctacctcac agtcagtagt gacatcccac aggccatctg ttcccaggac tagcacatca    420
tctgggcagt gctcatattg tgtc                                          444
```

<210> SEQ ID NO 8
<211> LENGTH: 428
<212> TYPE: DNA
<213> ORGANISM: Homo sapiens

<400> SEQUENCE: 8

| | | | | | |
|---|---|---|---|---|---|
| tttcctttat | ccatctcgtt | tatttgccaa | tagctgtaat | tttggatata | gcggacatcc | 60 |
| cttcttcagt | taagttgcca | ctaaagaagg | gtcagggaga | caacttcaga | atttgggctg | 120 |
| tgagaggagt | aagtatggag | aggctagtgg | gagggatggt | gttcagcccc | tcaggagtaa | 180 |
| ctgcctggcc | ctcccagggg | gatgacgaag | acagagatgt | catccccgga | acccagcttg | 240 |
| ttgttgggga | gacgccagcc | acggtctcgg | ggggtacccc | gggcccccag | gaccagagct | 300 |
| tgggccagag | ctgtatacct | gctgtggtca | ttaggctcat | aggccgacag | caccctgtcc | 360 |
| acagtggcag | ctacctcaca | gtcagtagtg | acatcccaca | ggccatctgt | tcccaggact | 420 |
| agcacatc | | | | | | 428 |

<210> SEQ ID NO 9
<211> LENGTH: 428
<212> TYPE: DNA
<213> ORGANISM: Homo sapiens

<400> SEQUENCE: 9

| | | | | | |
|---|---|---|---|---|---|
| tttcctttat | ccatctcgtt | tatttgccaa | tagctgtaat | tttggatata | gcggacatcc | 60 |
| cttcttcagt | taagttgcca | ctaaagaagg | gtcagggaga | caacttcaga | atttgggctg | 120 |
| tgagaggagt | aagtatggag | aggctagtgg | gagggatggt | gttcagcccc | tcaggagtaa | 180 |
| ctgcctggcc | ctcccagggg | gatgacgaag | acagagatgt | catccccgga | acccagcttg | 240 |
| ttgttgggga | gacgccagcc | acggtctctg | ggggtacccc | gggcccccag | gaccagagct | 300 |
| tgggccagag | ctgtatacct | gctgtggtca | ttaggctcat | aggccgacag | caccctgtcc | 360 |
| acagtggcag | ctacctcaca | gtcagtagtg | acatcccaca | ggccatctgt | tcccaggact | 420 |
| agcacatc | | | | | | 428 |

<210> SEQ ID NO 10
<211> LENGTH: 424
<212> TYPE: DNA
<213> ORGANISM: Homo sapiens

<400> SEQUENCE: 10

| | | | | | |
|---|---|---|---|---|---|
| ttttatccat | ctcgtttatt | tgccaatagc | tgtaattttg | gatatagcgg | acatcccttc | 60 |
| ttcagttaag | ttgccactaa | agaagggtca | gggagacaac | ttcagaattt | gggctgtgag | 120 |
| aggagtaagt | atggagaggc | tagtgggagg | gatggtgttc | agcccctcag | gagtaactgc | 180 |
| ctggccctcc | caggggggatg | acgaagacag | agatgtcatc | cccggaaccc | agcttgttgt | 240 |
| tggggagacg | ccagccacgg | tctctgtggg | taccccgggc | ccccaggacc | agagcttggg | 300 |
| ccagagctgt | atacctgctg | tggacattag | gctcataggc | cgacagcacc | ctgtccacag | 360 |
| tggcagctac | ctcacagtca | gtagtgacat | cccacaggcc | atctgttccc | aggactagca | 420 |
| catc | | | | | | 424 |

<210> SEQ ID NO 11
<211> LENGTH: 390
<212> TYPE: DNA
<213> ORGANISM: Homo sapiens -continued

```
<400> SEQUENCE: 11
atgatccatt cgcgcaatca gccattacct gtgcttcggg agtatccgcg cgcatccgtt      60
gtttagttta ttcttcacta aggaatggtc aaggagcacc actgtcgact gtgccctgcg     120
agagtgatga cgtatccaga ggatagtgcg acgtatgcgg ccagtccctc aggagtaact     180
gcctggccct cccaggggga tgacgaagac agagatgtca tccccggaac ccagcttgtt     240
gttggggaga cgccagccac ggtctcgggg ggtaccccgg gccccagga ccagagcttg      300 ggccagagct gtatacctgc tgtggtcatt aggctcatag gccgacagca ccctgtccac     360
agtggcagct acctcacagt cagtagtgac                                      390

<210> SEQ ID NO 12
<211> LENGTH: 368
<212> TYPE: DNA
<213> ORGANISM: Homo sapiens
<220> FEATURE:
<221> NAME/KEY: misc_feature
<222> LOCATION: (197)..(197)
<223> OTHER INFORMATION: n=a, c, g or t

<400> SEQUENCE: 12
tttatccatc tcatttattt gccaatagct gtaattttgg atatagcgga catcccttct      60
tcagttaagt tgccactaaa gaagggtcag ggagacaact tcagaatttg ggctgtgaga     120
ggagtaagta tggagaggct agtgggaggg atggtgttca gccectcagg agtaactgcc     180 tggccctccc aggggnatg acgaagacag agatgtcatc cccggaaccc agcttgttgt     240
tggggagacg ccagccacgg tctcgggggg tacccgggcc cccaggacca gagcttgggc     300
cagagctgta tacctgctgt ggtcattagg ctcataggcc gacagcaccc tgtccacagt     360
ggcagcta                                                              368
```

REGULATION OF HUMAN PROTEIN PHOSPHATASE IIC-LIKE ENZYME

This application is a National Stage application of co-pending PCT application PCT/EP01/09558 filed Aug. 20, 2001, which was published in English under PCT Article 21(2) on Mar. 7, 2002, which claims the benefit of U.S. provisional application Ser. No. 60/228,758 filed Aug. 30, 2000 and 60/280,115 filed Apr. 2, 2001. These applications are incorporated herein by reference in their entireties.

TECHNICAL FIELD OF THE INVENTION

The invention relates to the regulation of human protein phosphatase IIC-like enzyme activity for therapeutic effects.

BACKGROUND OF THE INVENTION

The protein phosphorylation/dephosphorylation cycle is one of the major regulatory mechanisms employed by eukaryotic cells to control cellular activities. See U.S. Pat. No. 5,853,997. It is estimated that more than 10% of the active proteins in a typical mammalian cell are phosphorylated. During protein phosphorylation/dephosphorylation, phosphate groups are transferred from adenosine triphosphate molecules to a protein by protein kinases and are removed from the protein by protein phosphatases.

Protein phosphatases function in cellular signaling events that regulate cell growth and differentiation, cell-to-cell contacts, the cell cycle, and oncogenesis. Three protein phosphatase families have been identified as evolutionarily distinct. These include the serine/threonine phosphatases, the protein tyrosine phosphatases, and the acid/alkaline phosphatases (Carbonneau & Tonks, *Ann. Rev. Cell Biol.* 8, 463–93, 1992).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups: PP-I, PP-IIA, PP-IIB, and PP-IIC. PP-I dephosphorylates many of the proteins phosphorylated by cyclic AMP-dependent protein kinase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine kinases. PP-IIB, or calcineurin (Cn), is a $Ca^{+2}$-activated phosphatase; it is involved in the regulation of such diverse cellular functions as ion channel regulation, neuronal transmission, gene transcription, muscle glycogen metabolism, and lymphocyte activation. PP-IIC is a $Mg^{+2}$-dependent phosphatase which participates in a wide variety of functions, including regulating cyclic AMP-activated protein-kinase activity, $Ca^{+2}$-dependent signal transduction, tRNA splicing, and signal transmission related to heat shock responses. PP-IIC is a monomeric protein with a molecular mass of about 40–45 kD. One α and several β isoforms of PP-IIC have been identified (Wenk et al., *FEBS Lett.* 297, 135–38, 1992; Terasawa et al., *Arch. Biochem. Biophys.* 307, 342–49, 1993; and Kato et al., *Arch. Biochem. Biophys.* 318, 387–93, 1995).

Because of the importance of protein phosphatases in a variety of biological functions, there is a need in the art to identify additional protein phosphatases which can be regulated to provide therapeutic effects.

SUMMARY OF THE INVENTION

It is an object of the invention to provide reagents and methods of regulating a human protein phosphatase IIC-like enzyme. These and other objects of the invention are provided by one or more of the embodiments described below.

One embodiment of the invention is a protein phosphatase IIC-like enzyme polypeptide comprising an amino acid sequence selected from the group consisting of:
  amino acid sequences which are at least about 50% identical to the amino acid sequence shown in SEQ ID NO: 2; and
  the amino acid sequence shown in SEQ ID NO: 2.

Yet another embodiment of the invention is a method of screening for agents which decrease extracellular matrix degradation. A test compound is contacted with a protein phosphatase IIC-like enzyme polypeptide comprising an amino acid sequence selected from the group consisting of:
  amino acid sequences which are at least about 50% identical to the amino acid sequence shown in SEQ ID NO: 2; and
  the amino acid sequence shown in SEQ ID NO: 2.

Binding between the test compound and the protein phosphatase IIC-like enzyme polypeptide is detected. A test compound which binds to the protein phosphatase IIC-like enzyme polypeptide is thereby identified as a potential agent for decreasing extracellular matrix degradation. The agent can work by decreasing the activity of the protein phosphatase IIC-like enzyme.

Another embodiment of the invention is a method of screening for agents which decrease extracellular matrix degradation. A test compound is contacted with a polynucleotide encoding a protein phosphatase IIC-like enzyme polypeptide, wherein the polynucleotide comprises a nucleotide sequence selected from the group consisting of:
  nucleotide sequences which are at least about 50% identical to the nucleotide sequence shown in SEQ ID NO: 1; and
  the nucleotide sequence shown in SEQ ID NO: 1.

Binding of the test compound to the polynucleotide is detected. A test compound which binds to the polynucleotide is identified as a potential agent for decreasing extracellular matrix degradation. The agent can work by decreasing the amount of the protein phosphatase IIC-like enzyme through interacting with the protein phosphatase IIC-like enzyme mRNA.

Another embodiment of the invention is a method of screening for agents which regulate extracellular matrix degradation. A test compound is contacted with a protein phosphatase IIC-like enzyme polypeptide comprising an amino acid sequence selected from the group consisting of:
  amino acid sequences which are at least about 50% identical to the amino acid sequence shown in SEQ ID NO: 2; and
  the amino acid sequence shown in SEQ ID NO: 2.

A protein phosphatase IIC-like enzyme activity of the polypeptide is detected. A test compound which increases protein phosphatase IIC-like enzyme activity of the polypeptide relative to protein phosphatase IIC-like enzyme activity in the absence of the test compound is thereby identified as a potential agent for increasing extracellular matrix degradation. A test compound which decreases protein phosphatase IIC-like enzyme activity of the polypeptide relative to protein phosphatase IIC-like enzyme activity in the absence of the test compound is thereby identified as a potential agent for decreasing extracellular matrix degradation.

Even another embodiment of the invention is a method of screening for agents which decrease extracellular matrix degradation. A test compound is contacted with a protein phosphatase IIC-like enzyme product of a polynucleotide which comprises a nucleotide sequence selected from the group consisting of:

nucleotide sequences which are at least about 50% identical to the nucleotide sequence shown in SEQ ID NO: 1; and the nucleotide sequence shown in SEQ ID NO: 1.

Binding of the test compound to the protein phosphatase IIC-like enzyme product is detected. A test compound which binds to the protein phosphatase IIC-like enzyme product is thereby identified as a potential agent for decreasing extracellular matrix degradation.

Still another embodiment of the invention is a method of reducing extracellular matrix degradation. A cell is contacted with a reagent which specifically binds to a polynucleotide encoding a protein phosphatase IIC-like enzyme polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1; and the nucleotide sequence shown in SEQ ID NO: 1.

Protein phosphatase IIC-like enzyme activity in the cell is thereby decreased.

The invention thus provides reagents and methods for regulating human protein phosphatase IIC-like enzyme which can be used inter alia, to treat disorders associated with an increase in apoptosis, including AIDS and other infectious or genetic immunodeficiencies, neurodegenerative diseases, myelodysplasia, ischemic injuries, toxin-induced diseases, wasting diseases, viral infections, and osteoporosis; disorders associated with a decrease in apoptosis, including cancer; and inflammatory disorders.

BRIEF DESCRIPTION OF THE DRAWINGS

FIG. 1 shows the DNA-sequence encoding a protein phosphatase IIC-like enzyme polypeptide (SEQ ID NO:1).

FIG. 2 shows the amino acid sequence deduced from the DNA-sequence of FIG. 1 (SEQ ID NO:2).

FIG. 3 shows the DNA-sequence encoding a protein phosphatase IIC-like enzyme polypeptide (SEQ ID NO:3).

FIG. 4 shows the amino acid sequence of the protein identified by SwissProt Accession No. P49598 (SEQ ID NO:4).

FIG. 5 shows the DNA-sequence encoding a protein phosphatase IIC-like enzyme polypeptide (SEQ ID NO:5).

FIG. 6 shows the DNA-sequence encoding a protein phosphatase IIC-like enzyme polypeptide (SEQ ID NO:6).

FIG. 7 shows the DNA-sequence encoding a protein phosphatase IIC-like enzyme polypeptide (SEQ ID NO:7).

FIG. 8 shows the DNA-sequence encoding a protein phosphatase IIC-like enzyme polypeptide (SEQ ID NO:8).

FIG. 9 shows the DNA-sequence encoding a protein phosphatase IIC-like enzyme polypeptide (SEQ ID NO:9).

FIG. 10 shows the DNA-sequence encoding a protein phosphatase IIC-like enzyme polypeptide (SEQ ID NO:10).

FIG. 11 shows the DNA-sequence encoding a protein phosphatase IIC-like enzyme polypeptide (SEQ ID NO:11).

FIG. 12 shows the DNA-sequence encoding a protein phosphatase IIC-like enzyme polypeptide (SEQ ID NO:12).

FIG. 13 shows the BLASTP alignment of SEQ ID NO:2 against swiss|P49598|P2C4_ARATH (SEQ ID NO:4).

FIG. 14 shows the BLOCKS search result.

FIG. 15 shows the HMMPFAM alignment of SEQ ID NO:2 against pfam|hmm|PP2C.

FIG. 16 shows the relative expression of protein phosphatase IIC-like enzyme in various human tissues.

FIG. 17 shows the relative expression of protein phosphatase IIC-like enzyme in various human respiratory tissues and cells. Key: HBEC=cultured human bronchial epithelial cells; H441=Clara-like cells; SMC=cultured airway smooth muscle cells; SAE=cultured small airway epithelial cells; AII=primary cultured alveolar type II cells; PMN=polymorphonuclear leukocytes; Mono-monocytes; Cult. Mono=cultured monocytes (macrophage-like).

DETAILED DESCRIPTION OF THE INVENTION

The invention relates to an isolated polynucleotide encoding a protein phosphatase IIC-like enzyme polypeptide and being selected from the group consisting of:

a) a polynucleotide encoding a protein phosphatase IIC-like enzyme polypeptide comprising an amino acid sequence selected from the group consisting of:

b) amino acid sequences which are at least about 50% identical to the amino acid sequence shown in SEQ ID NO: 2; and the amino acid sequence shown in SEQ ID NO: 2.

c) a polynucleotide comprising the sequence of SEQ ID NO: 1;

d) a polynucleotide which hybridizes under stringent conditions to a polynucleotide specified in (a) and (b);

e) a polynucleotide the sequence of which deviates from the polynucleotide sequences specified in (a) to (c) due to the degeneration of the genetic code; and f) a polynucleotide which represents a fragment, derivative or allelic variation of a polynucleotide sequence specified in (a) to (d).

Furthermore, it has been discovered by the present applicant that a novel protein phosphatase IIC-like enzyme, particularly a human proteain phosphatase IIC-like enzyme, is a discovery of the present invention. Human protein phosphatase IIC-like enzyme is 25% identical over 279 amino acids to the protein identified with SwissProt Accession No. P49598 (SEQ ID NO:4) and annotated as "protein phosphatase 2C (PP2C)" (FIG. 13). The results of a BLOCKS search of human protein phosphatase IIC-like enzyme (SEQ ID NO:14) is shown in FIG. 14. HMMPFAM alignment of human protein phosphatase IIC-like enzyme against pfam|hmm|PP2C is shown in FIG. 15. The sequence encoding human protein phosphatase IIC-like enzyme (SEQ ID NO:3) contains multiple ESTs, which are shown in SEQ ID NOS:5–12, indicating that this coding sequence is expressed.

Human protein phosphatase IIC-like enzyme is expected to be useful for the same purposes as protein phosphatase IIC enzymes. Regulation of human protein phosphatase IIC-like enzyme can therefore be used to treat disorders such as diabetes, CNS disorders, cardiovascular disorders, COPD, and cancer.

Polypeptides

Protein phosphatase IIC-like enzyme polypeptides according to the invention comprise at least 6, 10, 15, 25, 50, 75, 100, 125, 150, 175, 200, 250, or 275 contiguous amino acids of SEQ ID NO:2 or a biologically active variant thereof, as defined below. A protein phosphatase IIC-like enzyme polypeptide of the invention therefore can be a portion of a protein phosphatase IIC-like enzyme molecule, a full-length protein phosphatase IIC-like enzyme molecule, or a fusion protein comprising all or a portion of a protein phosphatase IIC-like enzyme molecule.

Biologically Active Variants

Protein phosphatase IIC-like enzyme variants which are biologically active, i.e., retain a protein phosphatase IIC-like enzyme activity, also are protein phosphatase IIC-like enzyme polypeptides. Preferably, naturally or non-naturally occurring protein phosphatase IIC-like enzyme variants have amino acid sequences which are at least about 50, preferably about 55, 60, 70, more preferably about 75, 80, 85, 90, 95, 96, 97, 98, or 99% identical to an amino acid sequence shown in SEQ ID NO:2. Percent identity between a putative protein phosphatase IIC-like enzyme variant and an amino acid sequence of SEQ ID NO:2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity can be found using computer programs well known in the art, such as DNASTAR software. Whether an amino acid change results in a biologically active protein phosphatase IIC-like enzyme polypeptide can readily be determined by assaying for protein phosphatase IIC-like enzyme activity, as is known in the art and described, for example, in the specific examples below.

Fusion Proteins

Fusion proteins are useful for generating antibodies against protein phosphatase IIC-like enzyme amino acid sequences and for use in various assay systems. For example, fusion proteins can be used to identify proteins which interact with portions of a protein phosphatase IIC-like enzyme polypeptide, including its active site and phosphatase domains. Methods such as protein affinity chromatography or library-based assays for protein-protein interactions, such as the yeast two-hybrid or phage display systems, can be used for this purpose. Such methods are well known in the art and also can be used as drug screens.

A protein phosphatase IIC-like enzyme fusion protein comprises two protein segments fused together by means of a peptide bond. Contiguous amino acids for use in a fusion protein can be selected from the amino acid sequences shown in SEQ ID NO:2 or from a biologically active variant thereof, such as those described above. For example, the first protein segment can comprise at least 6, 10, 15, 25, 50, 75, 100, 125, 150, 175, 200, 250, or 275 contiguous amino acids of SEQ ID NO:2 or a biologically active variant thereof. Preferably, a fusion protein comprises the active site of the protein phosphatase IIC-like enzyme or the functional domains shown in FIG. 2. The first protein segment also can comprise full-length protein phosphatase IIC-like enzyme.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the protein phosphatase IIC-like enzyme polypeptide-encoding sequence and the heterologous protein sequence, so that the protein phosphatase IIC-like enzyme polypeptide can be cleaved and purified away from the heterologous moiety.

A fusion protein can be synthesized chemically, as is known in the art. Preferably, a fusion protein is produced by covalently linking two protein segments or by standard procedures in the art of molecular biology. Recombinant DNA methods can be used to prepare fusion proteins, for example, by making a DNA construct which comprises protein phosphatase IIC-like enzyme coding sequences disclosed herein in proper reading frame with nucleotides encoding the second protein segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human protein phosphatase IIC-like enzyme can be obtained using protein phosphatase IIC-like enzyme polynucleotides (described below) to make suitable probes or primers to screening cDNA expression libraries from other species, such as mice, monkeys, or yeast, identifying cDNAs which encode homologs of protein phosphatase IIC-like enzyme, and expressing the cDNAs as is known in the art.

Polynucleotides

A protein phosphatase IIC-like enzyme polynucleotide can be single- or double-stranded and comprises a coding sequence or the complement of a coding sequence for a protein phosphatase IIC-like enzyme polypeptide. A nucleotide sequences encoding the human protein phosphatase IIC-like enzyme polypeptide shown in SEQ ID NO:2 is shown in SEQ ID NO: 1.

Degenerate nucleotide sequences encoding human protein phosphatase IIC-like enzyme polypeptides, as well as homologous nucleotide sequences which are at least about 50, preferably about 55, 60, 65, 70, more preferably about 75, 80, 85, 90, 95, 96, 97, 98, or 99% identical to the protein phosphatase IIC-like enzyme coding sequence nucleotide sequence shown in SEQ ID NO:1 also are protein phosphatase IIC-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of protein phosphatase IIC-like enzyme polynucleotides which encode biologically active protein phosphatase IIC-like enzyme polypeptides also are protein phosphatase IIC-like enzyme polynucleotides.

Identification of Variants and Homologs

Variants and homologs of the protein phosphatase IIC-like enzyme polynucleotides disclosed above also are protein phosphatase IIC-like enzyme polynucleotides. Typically, homologous protein phosphatase IIC-like enzyme polynucleotide sequences can be identified by hybridization of candidate polynucleotides to known protein phosphatase IIC-like enzyme polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the protein phosphatase IIC-like enzyme polynucleotides disclosed herein can be identified by making suitable probes or primers and screening cDNA expression libraries from other species, such as mice, monkeys, or yeast. Human variants of protein phosphatase IIC-like enzyme polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human protein phosphatase IIC-like enzyme polynucleotides or protein phosphatase IIC-like enzyme polynucleotides of other species can therefore be identified, for example, by hybridizing a putative homologous protein phosphatase IIC-like enzyme polynucleotide with a polynucleotide having a nucleotide sequence of SEQ ID NO:1, 3, or 5–13 or the complement thereof to form a test hybrid. The melting temperature of the test hybrid is compared with the melting temperature of a hybrid comprising protein phosphatase IIC-like enzyme polynucleotides having perfectly complementary nucleotide sequences, and the number or percent of basepair mismatches within the test hybrid is calculated.

Nucleotide sequences which hybridize to protein phosphatase IIC-like enzyme polynucleotides or their complements following stringent hybridization and/or wash conditions are also protein phosphatase IIC-like enzyme polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a protein phosphatase IIC-like enzyme polynucleotide having a coding sequence disclosed herein and a polynucleotide sequence which is at least about 50, preferably about 75, 90, 96, or 98% identical to that nucleotide sequence can be calculated, for example, using the equation of Bolton and McCarthy, *Proc. Natl. Acad. Sci. U.S.A.* 48, 1390 (1962):

$$T_m = 81.5° C. -16.6(\log_{10}[Na^+]) + 0.41(\%G+C) - 0.63(\% \text{formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring protein phosphatase IIC-like enzyme polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction (PCR), or synthesized using an automatic synthesizer. Methods for isolating polynucleotides are routine and are known in the art. Any such technique for obtaining a polynucleotide can be used to obtain isolated protein phosphatase IIC-like enzyme polynucleotides. For example, restriction enzymes and probes can be used to isolate polynucleotide fragments which comprise protein phosphatase IIC-like enzyme nucleotide sequences. Isolated polynucleotides are in preparations which are free or at least 70, 80, or 90% free of other molecules.

Protein phosphatase IIC-like enzyme cDNA molecules can be made with standard molecular biology techniques, using protein phosphatase IIC-like enzyme mRNA as a template. Protein phosphatase IIC-like enzyme cDNA molecules can thereafter be replicated using molecular biology techniques known in the art and disclosed in manuals such as Sambrook et al. (1989). An amplification technique, such as PCR, can be used to obtain additional copies of protein phosphatase IIC-like enzyme polynucleotides, using either human genomic DNA or cDNA as a template.

Alternatively, synthetic chemistry techniques can be used to synthesize protein phosphatase IIC-like enzyme polynucleotides. The degeneracy of the genetic code allows alternate nucleotide sequences to be synthesized which will encode a protein phosphatase IIC-like enzyme polypeptide having, for example, the amino acid sequence shown in SEQ ID NO:2 or a biologically active variant thereof.

Obtaining Full-Length Polynucleotides

The partial sequences of SEQ ID NOS:1, 3, 5, 7, 9, 11, 13, and 15 or their complements can be used to identify the corresponding full length gene from which they were derived. The partial sequences can be nick-translated or end-labeled with $^{32}P$ using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., 1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected and expanded, and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease III digestion (McCombie et al., *Methods* 3, 33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences encoding the disclosed portions of human protein phosphatase IIC-like enzyme to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Metliods Applic.* 1, 111–119, 1991). In this method, multiple restriction enzyme digestions and ligations are used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Protein phosphatase IIC-like enzyme polypeptides can be obtained, for example, by purification from cells, by expression of protein phosphatase IIC-like enzyme polynucleotides, or by direct chemical synthesis.

Protein Purification

Protein phosphatase IIC-like enzyme polypeptides can be purified from cells, including cells which have been transfected with protein phosphatase IIC-like enzyme expression constructs. Human fetal lung, testis, B-cells, and kidney tumors are especially useful sources of protein phosphatase IIC-like enzyme polypeptides. A purified protein phosphatase IIC-like enzyme polypeptide is separated from other compounds which normally associate with the protein phosphatase IIC-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified protein phosphatase IIC-like enzyme polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described in the specific examples, below.

Expression of Polynucleotides

To express a protein phosphatase IIC-like enzyme polypeptide, a protein phosphatase IIC-like enzyme polynucleotide can be inserted into an expression vector which contains the necessary elements for the transcription and translation of the inserted coding sequence. Methods which are well known to those skilled in the art can be used to construct expression vectors containing sequences encoding protein phosphatase IIC-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a protein phosphatase IIC-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a protein phosphatase IIC-like enzyme polypeptide, vectors based on SV40 or EBV can be used with an appropriate selectable marker.

Bacterial and Yeast Expression Systems

In bacterial systems, a number of expression vectors can be selected depending upon the use intended for the protein phosphatase IIC-like enzyme polypeptide. For example, when a large quantity of a protein phosphatase IIC-like enzyme polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene), in which the sequence encoding the protein phosphatase IIC-like enzyme polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989 or pGEX vectors (Promega, Madison, Wis.) can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or Factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding protein phosphatase IIC-like enzyme polypeptides can be driven by any of a number of promoters. For example, viral promoters such as the $^{35}S$ and 19S promoters of CaMV can be used alone or in combination with the omega leader sequence from TMV (Takamatsu *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (see, for example, Hobbs or Murray, in MCGRAW HILL YEARBOOK OF SCIENCE AND TECHNOLOGY, McGraw Hill, New York, N.Y., pp. 191–196, 1992).

An insect system also can be used to express a protein phosphatase IIC-like enzyme polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding protein phosphatase IIC-like enzyme polypeptides can be cloned into a non-essential region of the virus, such as the polyhedrin gene, and placed under control of the polyhedrin promoter. Successful insertion of protein phosphatase IIC-like enzyme polypeptides will render the polyhedrin gene inactive and produce recombinant virus lacking coat protein. The recombinant viruses can then be used to infect, for example, *S. frugiperda* cells or *Trichoplusia* larvae in which protein phosphatase IIC-like enzyme polypeptides can be expressed (Engelhard et al., *Proc. Nat. Acad. Sci.* 91, 3224–3227, 1994).

Mammalian Expression Systems

A number of viral-based expression systems can be utilized in mammalian host cells. For example, if an adenovirus is used as an expression vector, sequences encoding protein phosphatase IIC-like enzyme polypeptides can be ligated into an adenovirus transcription/translation complex consisting of the late promoter and tripartite leader sequence. Insertion in a non-essential E1 or E3 region of the viral genome can be used to obtain a viable virus which is capable of expressing a protein phosphatase IIC-like enzyme polypeptide in infected host cells (Logan & Shenk, *Proc. Natl. Acad. Sci.* 81, 3655–3659, 1984). In addition, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding protein phosphatase IIC-like enzyme polypeptides. Such signals include the ATG initiation codon and adjacent sequences. In cases where sequences encoding a protein phosphatase IIC-like enzyme polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process an expressed protein phosphatase IIC-like enzyme polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and charac-teristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express protein phosphatase IIC-like enzyme polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced protein phosphatase IIC-like enzyme sequences. Resistant clones of stably transformed cells can be proliferated using tissue culture techniques appropriate to the cell type.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980). Genes which can be employed in tk or aprf cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980); npt confers resistance to the aminoglycosides, neomycin and G-418 (Colbere-Garapin et al., *J. Mol. Biol.* 150, 1–14, 1981); and als and pat confer resistance to chlorsulfuron and phosphinotricin acetyltransferase, respectively (Murray, 1992 supra). Additional selectable genes have been described, for example trpB, which allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression of Polypeptides

Although the presence of marker gene expression suggests that the protein phosphatase IIC-like enzyme polynucleotide is also present, its presence and expression may need to be confirmed. For example, if a sequence encoding a protein phosphatase IIC-like enzyme polypeptide is inserted within a marker gene sequence, transformed cells containing sequences which encode a protein phosphatase IIC-like enzyme polypeptide can be identified by the absence of marker gene function. Alternatively, a marker gene can be placed in tandem with a sequence encoding a protein phosphatase IIC-like enzyme polypeptide under the control of a single promoter. Expression of the marker gene in response to induction or selection usually indicates expression of the protein phosphatase IIC-like enzyme polynucleotide.

Alternatively, host cells which contain a protein phosphatase IIC-like enzyme polynucleotide and which express a protein phosphatase IIC-like enzyme polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein.

The presence of a polynucleotide sequence encoding a protein phosphatase IIC-like enzyme polypeptide can be detected by DNA-DNA or DNA-RNA hybridization or amplification using probes or fragments or fragments of polynucleotides encoding a protein phosphatase IIC-like enzyme polypeptide. Nucleic acid amplification-based assays involve the use of oligonucleotides selected from sequences encoding a protein phosphatase IIC-like enzyme polypeptide to detect transformants which contain a protein phosphatase IIC-like enzyme polynucleotide.

A variety of protocols for detecting and measuring the expression of a protein phosphatase IIC-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a protein phosphatase IIC-like enzyme polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding protein phosphatase IIC-like enzyme polypeptides include oligolabeling, nick translation, end-labeling, or PCR amplification using a labeled nucleotide. Alternatively, sequences encoding a protein phosphatase IIC-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding a protein phosphatase IIC-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode protein phosphatase IIC-like enzyme polypeptides can be designed to contain signal sequences which direct secretion of protein phosphatase IIC-like enzyme polypeptides through a prokaryotic or eukaryotic cell membrane. Other constructions can be used to join a sequence encoding a protein phosphatase IIC-like enzyme polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the protein phosphatase IIC-like enzyme polypeptide can be used to facilitate purification. One such expression vector provides for expression of a fusion protein containing a protein phosphatase IIC-like enzyme polypeptide and 6 histidine residues preceding a thioredoxin or an enterokinase cleavage site. The histidine residues facilitate purification on IMAC (immobilized metal ion affinity chromatography as described in Porath et al., *Prot. Exp. Purif* 3, 263–281, 1992), while the enterokinase cleavage site provides a means for purifying the protein phosphatase IIC-like enzyme polypeptide from the fusion protein. Vectors which contain fusion proteins are disclosed in Kroll et al., *DNA Cell Biol.* 12, 441–453, 1993).

Chemical Synthesis

Sequences encoding a protein phosphatase IIC-like enzyme polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a protein phosphatase IIC-like enzyme polypeptide itself can be produced using chemical methods to synthesize its amino acid sequence. For example, protein phosphatase IIC-like enzyme polypeptides can be produced by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Various fragments of protein phosphatase IIC-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic protein phosphatase IIC-like enzyme polypeptide can be confirmed by amino acid analysis or sequencing (e.g., the Edman degradation procedure; see Creighton, supra). Additionally, any portion of the amino acid sequence of the protein phosphatase IIC-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce protein phosphatase IIC-like enzyme polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter protein phosphatase IIC-like enzyme polypeptide-encoding sequences for a variety of reasons, including modification of the cloning, processing, and/or expression of the gene product. DNA shuffling by random fragmentation and PCR reassembly of gene fragments and synthetic oligonucleotides can be used to engineer the nucleotide sequences. For example, site-directed muta-genesis can be used to insert new restriction sites, alter glycosylation patterns, change codon preference, produce splice variants, introduce mutations, and so forth.

Antibodies

Any type of antibody known in the art can be generated to bind specifically to an epitope of a protein phosphatase IIC-like enzyme polypeptide. "Antibody" as used herein includes intact immunoglobulin molecules, as well as fragments thereof, such as Fab, F(ab')$_2$, and Fv, which are capable of binding an epitope of a protein phosphatase IIC-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a protein phosphatase IIC-like enzyme polypeptide can be used therapeutically, as well as in immunochemical assays, including but not limited to Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a protein phosphatase IIC-like enzyme polypeptide provides a detection signal at least 5-, 10-, or 20-fold higher than a detection signal provided with other proteins when used in an immuno-chemical assay. Preferably, antibodies which specifically bind to protein phosphatase IIC-like enzyme polypeptides do not detect other proteins in immuno-chemical assays and can immunoprecipitate a protein phosphatase IIC-like enzyme polypeptide from solution.

Protein phosphatase IIC-like enzyme polypeptides can be used to immunize a mammal, such as a mouse, rat, rabbit, guinea pig, monkey, or human, to produce polyclonal antibodies. If desired, a protein phosphatase IIC-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a protein phosphatase IIC-like enzyme polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, one can produce humanized antibodies using recombinant methods, as described in GB2188638B. Antibodies which specifically bind to a protein phosphatase IIC-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to protein phosphatase IIC-like enzyme polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61, 497–501; Nicholls et al., 1993, *J. Immunol. Meth.* 165, 81–91.

Antibodies which specifically bind to protein phosphatase IIC-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies of the invention can be purified by methods well known in the art. For example, antibodies can be affinity purified by passage over a column to which a protein phosphatase IIC-like enzyme polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of protein phosphatase IIC-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of protein phosphatase IIC-like enzyme gene expression can be obtained by designing antisense oligonucleotides which will form duplexes to the control, 5', or regulatory regions of the protein phosphatase IIC-like enzyme gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g. Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful duplex formation between an antisense oligonucleotide and the complementary sequence of a protein phosphatase IIC-like enzyme polynucleotide. Antisense oligonucleotides which comprise, for example, 2, 3, 4, or 5 or more stretches of contiguous nucleotides which are precisely complementary to a protein phosphatase IIC-like enzyme polynucleotide, each separated by a stretch of contiguous nucleotides which are not complementary to adjacent protein phosphatase IIC-like enzyme nucleotides, can provide targeting specificity for protein phosphatase IIC-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular protein phosphatase IIC-like enzyme polynucleotide sequence.

Antisense oligonucleotides can be modified without affecting their ability to hybridize to a protein phosphatase IIC-like enzyme polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a protein phosphatase IIC-like enzyme polynucleotide can be used to generate ribozymes which will specifically bind to mRNA transcribed from the protein phosphatase IIC-like enzyme polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a protein phosphatase IIC-like enzyme RNA target are initially identified by scanning the RNA molecule for ribozyme cleavage sites which include the following sequences: GUA, GUU, and GUC. Once identified, short RNA sequences of between 15 and 20 ribonucleotides corresponding to the region of the protein phosphatase IIC-like enzyme target RNA containing the cleavage site can be evaluated for secondary structural features which may render the target inoperable. The suitability of candidate targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related; thus, upon hybridizing to the protein phosphatase IIC-like enzyme target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease protein phosphatase IIC-like enzyme expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of protein phosphatase IIC-like enzyme mRNA occurs only when both a ribozyme and a target gene are induced in the cells.

Identification of Target and Pathway Genes and Proteins

Described herein are methods for the identification of genes whose products interact with human protein phosphatase IIC-like enzyme-like enzyme. Such genes may represent genes which are differentially expressed in disorders including, but not limited to, diabetes, CNS disorders, cardiovascular disorders, COPD, and cancer. Further, such genes may represent genes which are differentially regulated in response to manipulations relevant to the progression or treatment of such diseases. Such differentially expressed genes may represent "target" and/or "fingerprint" genes. Methods for the identification of such differentially expressed genes are described below. Methods for the further characterization of such differentially expressed genes, and for their identification as target and/or fingerprint genes also are described below.

In addition, methods are described for the identification of genes, termed "pathway genes," which are involved in a disorder of interest. "Pathway gene," as used herein, refers to a gene whose gene product exhibits the ability to interact with gene products involved in these disorders. A pathway gene may be differentially expressed and, therefore, may have the characteristics of a target and/or fingerprint gene.

"Differential expression" refers to both quantitative as well as qualitative differences in a gene's temporal and/or tissue expression pattern. Thus, a differentially expressed gene may qualitatively have its expression activated or completely inactivated in normal versus diseased states, or under control versus experimental conditions. Such a qualitatively regulated gene will exhibit an expression pattern within a given tissue or cell type which is detectable in either normal or diseased subjects, but is not detectable in both. Alternatively, such a qualitatively regulated gene will exhibit an expression pattern within a given tissue or cell type which is detectable in either control or experimental subjects, but is not detectable in both. "Detectable" refers to an RNA expression pattern which is detectable via the standard techniques of differential display, RT-PCR and/or Northern analyses, which are well known to those of skill in the art.

A differentially expressed gene may have its expression modulated, i.e., quantitatively increased or decreased, in normal versus diseased states, or under control versus experimental conditions. The degree to which expression differs in a normal versus a diseased state need only be large enough to be visualized via standard characterization techniques, such as, for example, the differential display technique described below. Other such standard characterization techniques by which expression differences may be visualized include but are not limited to, quantitative RT (reverse transcriptase) PCR and Northern analyses.

Differentially expressed genes may be further described as target genes and/or fingerprint genes. "Fingerprint gene" refers to a differentially expressed gene whose expression pattern may be utilized as part of a prognostic or diagnostic evaluation, or which, alternatively, may be used in methods for identifying compounds useful for the treatment of various disorders. A fingerprint gene may also have the characteristics of a target gene or a pathway gene.

"Target gene" refers to a differentially expressed gene involved in a disorder of interest by which modulation of the level of target gene expression or of target gene product activity may act to ameliorate symptoms. A target gene may also have the characteristics of a fingerprint gene and/or a pathway gene.

Identification of Differentially Expressed Genes

A variety of methods may be utilized for the identification of genes which are involved in a disorder of interest. To identify differentially expressed genes, RNA, either total or mRNA, may be isolated from one or more tissues of the subjects utilized in paradigms such as those described above. RNA samples are obtained from tissues of experimental subjects and from corresponding tissues of control subjects. Any RNA isolation technique which does not select against the isolation of mRNA may be utilized for the purification of such RNA samples. See, for example, Ausubel et al., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples which represent RNA produced by differentially expressed genes may be identified by utilizing a variety of methods which are well known to those of skill in the art. For example, differential screening (Tedder et al., Proc. Natl. Acad. Sci. USA. 85, 208–12, 1988), subtractive hybridization (Hedrick et al., Nature 308, 149–53; Lee et al., Proc. Natl. Acad. Sci. U.S.A. 88, 2825, 1984), and, preferably, differential display (Liang & Pardee, Science 257, 967–71, 1992; U.S. Pat. No. 5,262,311), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type or tissue derived from a control subject, while the second cDNA probe may correspond to a total cell cDNA probe of the same cell type or tissue derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue or cell type, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the is construction of a library comprising clones derived from differentially expressed genes.

The differential display technique describes a procedure, utilizing the well known polymerase chain reaction (PCR; the experimental embodiment set forth in Mullis, U.S. Pat. No. 4,683,202), which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers.

Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The 3' oligonucleotide primer of the primer pairs may contain an oligo dT stretch of 10–13, preferably 11, dT nucleotides at its 5' end, which hybridizes to the poly(A) tail of mRNA or to the complement of a cDNA reverse transcribed from an mRNA poly(A) tail. Second, in order to increase the specificity of the 3' primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer may contain a nucleotide sequence expected, statistically, to have the ability to hybridize to cDNA sequences derived from the tissues of interest. The nucleotide sequence may be an arbitrary one, and the length of the 5' oligonucleotide primer may range from about 9 to about 15 nucleotides, with about 13 nucleotides being preferred. Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differentially expressed genes are indicated by differences in the two banding patterns.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis, quantitative RT PCR or RNase protection. Upon corroboration, the differentially expressed genes may be further characterized, and may be identified as target and/or fingerprint genes, as discussed below.

Amplified sequences of differentially expressed genes obtained through, for example, differential display may be used to isolate full length clones of the corresponding gene. The full length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate full length cDNA sequences. As described above, the isolated, amplified gene fragments obtained through differential display have 5' terminal ends at some random point within the gene and usually have 3' terminal ends at a position corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of full length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, and Ausubel et al., 1989.

Identification of Pathway Genes

Methods are described herein for the identification of pathway genes. "Pathway gene" refers to a gene whose gene product exhibits the ability to interact with gene products involved in a disorder of interest. A pathway gene may be differentially expressed and, therefore, may have the characteristics of a target and/or fingerprint gene.

Any method suitable for detecting protein-protein interactions may be employed for identifying pathway gene products by identifying interactions between gene products and gene products known to be involved in a disorder of interest. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, PROTEINS: STRUCTURES AND MOLECULAR PRINCIPLES, W. H. Freeman & Co., N.Y., pp. 34–49, 1983). The amino acid sequence obtained may be used as a guide for the generation of oligonucleotide mixtures that can be used to screen for pathway gene sequences. Screening made be accomplished, for example, by standard hybridization or PCR techniques. Techniques for the generation of oligonucleotide mixtures and the screening are well-known. (see, e.g., Ausubel, 1989, and Innis et al., eds., PCR PROTOCOLS: A GUIDE TO METHODS AND APPLICATIONS, 1990, Academic Press, Inc., New York).

Methods may be employed which result in the simultaneous identification of pathway genes which encode the protein interacting with a protein involved in a disorder of interest. These methods include, for example, probing expression libraries with labeled protein known or suggested to be involved in such disorders, using this protein in a manner similar to the well known technique of antibody probing of λgt11 libraries.

One method which detects protein interactions in vivo, the two-hybrid system, is described in detail for illustration only and not by way of limitation. One version of this system is been described in Chien et al., 1991, *Proc. Natl. Acad. Sci. U.S.A.* 88, 9578–82, 1991, and is commercially available from Clontech (Palo Alto, Calif.). Briefly, utilizing such a system, plasmids are constructed that encode two hybrid proteins: one consists of the DNA-binding domain of a transcription activator protein fused to a known protein, in this case, a protein known to be involved in a disorder of interest and the other consists of the transcription activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with a known "bait" gene product. By way of example, and not by way of limitation, gene products known to be involved in a disorder of interest may be used as the bait gene products. These include but are not limited to the intracellular domain of receptors for such hormones as neuropeptide Y, galanin, interostatin, insulin, and CCK. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait gene product are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GALA activation domain, that interacts with bait gene product will reconstitute an active GALA protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art. Once a pathway gene has been identified and isolated, it may be further characterized, as described below.

Characterization of Differentially Expressed and Pathway Genes

Differentially expressed and pathway genes, such as those identified via the methods discussed above, as well as genes identified by alternative means, may be further characterized by utilizing, for example, methods such as those discussed herein. Such genes will be referred to herein as "identified genes." Analyses such as those described herein, yield information regarding the biological function of the identified genes. An assessment of the biological function of the differentially expressed genes, in addition, will allow for their designation as target and/or fingerprint genes.

Specifically, any of the differentially expressed genes whose further characterization indicates that a modulation of the gene's expression or a modulation of the gene product's activity may ameliorate any of the disorders of interest will be designated "target genes," as defined above. Such target genes and target gene products, along with those discussed below, will constitute the focus of the compound discovery strategies discussed below. Further, such target genes, target gene products and/or modulating compounds can be used as part of the treatment methods described below.

Any of the differentially expressed genes whose further characterization indicates that such modulations may not positively affect a disorder of interest, but whose expression pattern contributes to a gene expression "fingerprint" pattern correlative of, for example, a malignant state will be designated a "fingerprint gene." It should be noted that each of the target genes may also function as fingerprint genes, as well as may all or a portion of the pathway genes.

Pathway genes may also be characterized according to techniques such as those described herein. Those pathway genes which yield information indicating that they are differentially expressed and that modulation of the gene's expression or a modulation of the gene product's activity may ameliorate any of the disorders of interest will be also be designated "target genes." Such target genes and target gene products, along with those discussed above, will constitute the focus of the compound discovery strategies discussed below and can be used as part of treatment methods.

Characterization of one or more of the pathway genes may reveal a lack of differential expression, but evidence that modulation of the gene's activity or expression may, nonetheless, ameliorate symptoms. In such cases, these genes and gene products would also be considered a focus of the compound discovery strategies. In instances wherein a pathway gene's characterization indicates that modulation of gene expression or gene product activity may not positively affect disorders of interest, but whose expression is differentially expressed and contributes to a gene expression fingerprint pattern correlative of, for example, cancer, such pathway genes may additionally be designated as fingerprint genes.

A variety of techniques can be utilized to further characterize the identified genes. First, the nucleotide sequence of the identified genes, which may be obtained by utilizing standard techniques well known to those of skill in the art, may, for example, be used to reveal homologies to one or more known sequence motifs which may yield information regarding the biological function of the identified gene product.

Second, an analysis of the tissue and/or cell type distribution of the mRNA produced by the identified genes may be conducted, utilizing standard techniques well known to those of skill in the art. Such techniques may include, for example, Northern, RNase protection and RT-PCR analyses. Such analyses provide information as to, for example, whether the identified genes are expressed in tissues or cell types expected to contribute to the disorders of interest. Such analyses may also provide quantitative information regarding steady state mRNA regulation, yielding data concerning which of the identified genes exhibits a high level of regulation in, preferably, tissues which may be expected to contribute to the disorders of interest. Additionally, standard in situ hybridization techniques may be utilized to provide information regarding which cells within a given tissue express the identified gene. Such an analysis may provide information regarding the biological function of an identified gene relative to a given disorder in instances wherein only a subset of the cells within the tissue is thought to be relevant to the disorder.

Third, the sequences of the identified genes may be used, utilizing standard techniques, to place the genes onto genetic maps, e.g., mouse (Copeland and Jenkins, *Trends in Genetics* 7, 113–18, 1991) and human genetic maps (Cohen et al., *Nature* 366, 698–701, 1993). Such mapping information may yield information regarding the genes' importance to human disease by, for example, identifying genes which map within genetic regions to which known genetic disorders map.

Fourth, the biological function of the identified genes may be more directly assessed by utilizing relevant in vivo and in vitro systems. In vivo systems may include, but are not limited to, animal systems which naturally exhibit symptoms of interest, or ones which have been engineered to exhibit such symptoms. Further, such systems may include systems for the further characterization of a disorder of interest and may include, but are not limited to, naturally occurring and transgenic animal systems. In vitro systems may include, but are not limited to, cell-based systems comprising cell types known or suspected of contributing to the disorder of interest. Such cells may be wild type cells, or may be non-wild type cells containing modifications known to, or suspected of, contributing to the disorder of interest.

In further characterizing the biological function of the identified genes, the expression of these genes may be modulated within the in vivo and/or in vitro systems, i.e., either overexpressed or underexpressed in, for example, transgenic animals and/or cell lines, and its subsequent effect on the system then assayed. Alternatively, the activity of the product of the identified gene may be modulated by either increasing or decreasing the level of activity in the in vivo and/or in vitro system of interest, and its subsequent effect then assayed.

The information obtained through such characterizations may suggest relevant methods for the treatment of disorders involving the gene of interest. Further, relevant methods for the treatment of such disorders involving the gene of interest may be suggested by information obtained from such characterizations. For example, treatment may include a modulation of gene expression and/or gene product activity. Characterization procedures such as those described herein may indicate where such modulation should involve an increase or a decrease in the expression or activity of the gene or gene product of interest.

Screening Methods

The invention provides methods for identifying modulators, i.e., candidate or test compounds which bind to protein phosphatase IIC-like enzyme polypeptides or polynucleotides and/or have a stimulatory or inhibitory effect on, for example, expression or activity of the protein phosphatase IIC-like enzyme polypeptide or polynucleotide, so as to regulate degradation of the extracellular matrix. Decreased extracellular matrix degradation is useful for preventing or suppressing malignant cells from metastasizing. Increased extracellular matrix degradation may be desired, for example, in developmental disorders characterized by inappropriately low levels of extracellular matrix degradation or in regeneration.

The invention provides assays for screening test compounds which bind to or modulate the activity of a protein phosphatase IIC-like enzyme polypeptide or a protein phosphatase IIC-like enzyme polynucleotide. A test compound preferably binds to a protein phosphatase IIC-like enzyme polypeptide or polynucleotide. More preferably, a test compound decreases a protein phosphatase IIC-like enzyme activity of a protein phosphatase IIC-like enzyme polypeptide or expression of a protein phosphatase IIC-like enzyme polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to protein phosphatase IIC-like enzyme polypeptides or polynucleotides or to affect protein phosphatase IIC-like enzyme activity or protein phosphatase IIC-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad Sc. USA.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies the active site or the fad-like domain of the protein phosphatase IIC-like enzyme polypeptide, thereby making the active site or phosphatase domains inaccessible to substrate such that normal biological activity is prevented. Examples of such small molecules include, but are not limited to, small peptides or peptide-like molecules. In binding assays, either the test compound or the protein phosphatase IIC-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the protein phosphatase IIC-like enzyme polypeptide can then be accomplished, for example, by direct counting of radioemmission, by scintillation counting, or by determining conversion of an appropriate substrate to a detectable product.

Alternatively, binding of a test compound to a protein phosphatase IIC-like enzyme polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a protein phosphatase IIC-like enzyme polypeptide. (McConnell et al., *Science* 257, 1906–1912, 1992).

Determining the ability of a test compound to bind to a protein phosphatase IIC-like enzyme polypeptide also can be accomplished using a technology such as real-time Bimolecular Interaction Analysis (BIA). Sjolander & Urbaniczky, *Anal. Chem.* 63, 2338–2345, 1991, and Szabo et al., *Curr. Opin. Struct. Biol.* 5, 699–705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a protein phosphatase IIC-like enzyme polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the protein phosphatase IIC-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding a protein phosphatase IIC-like enzyme polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form a protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the protein phosphatase IIC-like enzyme polypeptide.

It may be desirable to immobilize either the protein phosphatase IIC-like enzyme polypeptide (or polynucleotide) or the test compound to facilitate separation of bound from unbound forms of one or both of the interactants, as well as to accommodate automation of the assay. Thus, either the protein phosphatase IIC-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the protein phosphatase IIC-like enzyme polypeptide (or polynucleotide) or test compound to a solid support, including use of covalent and non-covalent linkages, passive absorption, or pairs of binding moieties attached respectively to the polypeptide or test compound and the solid support. Test compounds are preferably bound to the solid support in an array, so that the location of individual test compounds can be tracked. Binding of a test compound to a protein phosphatase IIC-like enzyme polypeptide (or polynucleotide) can be accomplished in any vessel suitable for containing the reactants. Examples of such vessels include microtiter plates, test tubes, and microcentrifuge tubes.

In one embodiment, a protein phosphatase IIC-like enzyme polypeptide is a fusion protein comprising a domain that allows the protein phosphatase IIC-like enzyme polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed protein phosphatase IIC-like enzyme polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either a protein phosphatase IIC-like enzyme polypeptide (or polynucleotide) or a test compound can be immobilized utilizing conjugation of biotin and streptavidin. Biotinylated protein phosphatase IIC-like enzyme polypeptides or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a protein phosphatase IIC-like enzyme polypeptide polynucleotides, or a test compound, but which do not interfere with a desired binding site, such as the active site or a phosphatase domain of the protein phosphatase IIC-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the protein phosphatase IIC-like enzyme polypeptide (or polynucleotides) or test compound, enzyme-linked assays which rely on detecting a protein phosphatase IIC-like enzyme activity of the protein phosphatase IIC-like enzyme polypeptide, and SDS gel electrophoresis under non-reducing conditions.

Screening for test compounds which bind to a protein phosphatase IIC-like enzyme polypeptide or polynucleotide also can be carried out in an intact cell. Any cell which comprises a protein phosphatase IIC-like enzyme polynucleotide or polypeptide can be used in a cell-based assay system. A protein phosphatase IIC-like enzyme polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA468, SK-BR3, and BT-474, the A549 lung cancer cell line, and the H392 glioblastoma cell line, can be used. An intact cell is contacted with a test compound. Binding of the test compound to a protein phosphatase IIC-like enzyme polypeptide or polynucleotide is determined as described above, after lysing the cell to release the protein phosphatase IIC-like enzyme polypeptide- or polynucleotide-test compound complex.

Enzyme Assays

Test compounds can be tested for the ability to increase or decrease a protein phosphatase IIC-like enzyme activity of a protein phosphatase IIC-like enzyme polypeptide. Protein phosphatase IIC-like enzyme activity can be measured, for example, using the methods described in the specific examples, below. Protein phosphatase IIC-like enzyme activity can be measured after contacting either a purified protein phosphatase IIC-like enzyme polypeptide, a cell extract, or an intact cell with a test compound. A test compound which decreases protein phosphatase IIC-like enzyme activity by at least about 10, preferably about 50, more preferably about 75, 90, or 100% is identified as a potential therapeutic agent for decreasing human protein phosphatase IIC-like enzyme activity. A test compound which increases protein phosphatase IIC-like enzyme activity by at least about 10, preferably about 50, more preferably about 75, 90, or 100% is identified as a potential therapeutic agent for increasing human protein phosphatase IIC-like enzyme activity.

Gene Expression

In another embodiment, test compounds which increase or decrease protein phosphatase IIC-like enzyme gene expression are identified. A protein phosphatase IIC-like enzyme polynucleotide is contacted with a test compound, and the expression of an RNA or polypeptide product of the protein phosphatase IIC-like enzyme polynucleotide is determined. The level of expression of protein phosphatase IIC-like enzyme mRNA or polypeptide in the presence of the test compound is compared to the level of expression of protein phosphatase IIC-like enzyme mRNA or polypeptide in the absence of the test compound. The test compound can then be identified as a modulator of expression based on this comparison. For example, when expression of protein phosphatase IIC-like enzyme mRNA or polypeptide is greater in the presence of the test compound than in its absence, the test compound is identified as a stimulator or enhancer of protein phosphatase IIC-like enzyme mRNA or polypeptide is less expression. Alternatively, when expression of the mRNA or protein is less in the presence of the test compound than in its absence, the test compound is identified as an inhibitor of protein phosphatase IIC-like enzyme mRNA or polypeptide expression.

The level of protein phosphatase IIC-like enzyme mRNA or polypeptide expression in the cells can be determined by methods well known in the art for detecting mRNA or protein. Either qualitative or quantitative methods can be used. The presence of polypeptide products of a protein phosphatase IIC-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a protein phosphatase IIC-like enzyme polypeptide.

Such screening can be carried out either in a cell-free assay system or in an intact cell. Any cell which expresses a protein phosphatase IIC-like enzyme polynucleotide can be used in a cell-based assay system. The protein phosphatase IIC-like enzyme polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT474, the A549 lung cancer cell line, and the H392 glioblastoma cell line, can be used.

Pharmaceutical Compositions

The invention also provides pharmaceutical compositions which can be administered to a patient to achieve a therapeutic effect. Pharmaceutical compositions of the invention can comprise a protein phosphatase IIC-like enzyme polypeptide, protein phosphatase IIC-like enzyme polynucleotide, antibodies which specifically bind to a protein phosphatase IIC-like enzyme polypeptide, or mimetics, agonists, antagonists, or inhibitors of a protein phosphatase IIC-like enzyme polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well sown in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON×S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Diagnostic Methods

The human protein phosphatase IIC-like enzyme and polynucleotides encoding it can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding human protein phosphatase IIC-like enzyme in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and Sl protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of human protein phosphatase IIC-like enzyme also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

Therapeutic Indications and Methods

During fetal development, decreased expression of human protein phosphatase IIC-like enzyme may cause an increase in apoptosis with no adverse effects to the subject. However, in other situations and in adults, decreased expression of human protein phosphatase IIC-like enzyme may cause an increase in apoptosis which is detrimental to the subject. Therefore, in one embodiment, human protein phosphatase IIC-like enzyme or a portion or biologically active variant thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplasia syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. In another embodiment, an agonist which is specific for human protein phosphatase IIC-like enzyme may be used to prevent or treat a disorder associated with increased apoptosis including, but not limited to, those listed above. In still another embodiment, a vector capable of expressing human protein phosphatase IIC-like enzyme, or a fragment or a derivative thereof, may be used to prevent or treat a disorder associated with increased apoptosis including, but not limited to, those listed above.

Human protein phosphatase IIC-like enzyme agonists and antagonists may be used to mimic, augment or inhibit the action of the enzyme, which may be useful to treat diabetes. Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type 1 diabetes is initiated by an autoimuune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

Human protein phosphatase IIC-like enzyme agonists and antagonists also may be used to treat CNS disorders. CNS disorders which can be treated include brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it is possible to treat cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities, by regulating the activity of human protein phosphatase IIC-like enzyme.

Human protein phosphatase IIC-like enzyme agonists and antagonists also may be used to treat cardiovascular disorders. Cardiovascular diseases include the following disorders of the heart and the vascular system: congestive heart failure, myocardial infarction, ischemic diseases of the heart, all kinds of atrial and ventricular arrhythmias, hypertensive vascular diseases and peripheral vascular diseases.

Heart failure is defined as a pathophysiologic state in which an abnormality of cardiac function is responsible for the failure of the heart to pump blood at a rate commensurate with the requirement of the metabolizing tissue. It includes all forms of pumping failure such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in an perfusion which is inadequate to meet the myocardial requirement for oxygen. This group of diseases include stable angina, unstable angina and asymptomatic ischemia.

Arrhythmias include all forms of atrial and ventricular tachyarrhythmias (atrial tachycardia, atrial flutter, atrial fibrillation, atrio-ventricular reentrant tachycardia, preexcitation syndrome, ventricular tachycardia, ventricular flutter, ventricular fibrillation) as well as bradycardic forms of arrhythmias.

Hypertensive vascular diseases include primary as well as all kinds of secondary arterial hypertension (renal, endocrine, neurogenic, others). The genes may be used as drug targets for the treatment of hypertension as well as for the prevention of all complications.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Human protein phosphatase IIC-like enzyme agonists and antagonists also may be used to treat chronic obstructive pulmonary disease. Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Inhibition of protein phosphatases may have potential for the treatment of COPD. At least two aspects of the disease may be amenable to such an approach. Firstly, inhibition of PP2B has been demonstrated to increase the secretion of pulmonary surfactant by alveolar type II cells (Matthew et al, Am J. Physiol. 276: L786–951, 1999). As surfactant is key to the maintenance of airway patency, stimulation of surfactant secretion would be expected to improve the opening of small airways, resulting in more efficient gas conductance. Secondly, protein phosphatases may be involved in the maintenance of chronic airway inflammation prevalent in COPD. Inhibition of PP2B suppresses T cell activation (Lockhart et al., Brit. J. Pharmacol. 123: 879–89, 1998), and modulation of the activity of both PP2B and PP1/PP2A regulates the release of nitric oxide and secretion of tumour necrosis factor α and interleukin-10 from alveolar macrophages in response to lipopolysacharride and interferon γ(Boehringer et al., European Cytokine Network, 10: 211–8, 1999). Protein phosphatases, therefore, may play important roles in the pathogenesis of COPD and known and novel members represent attractive therapeutic targets for treatment of the disease.

Human protein phosphatase IIC-like enzyme agonists and antagonists also may be used to treat cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Human protein phosphatase IIC-like enzyme agonists and antagonists may be used to mimic, augment or inhibit the action of the enzyme, which may be useful to treat osteoporosis, Paget's disease, degradation of bone implants particularly dental implants. Osteoporosis is a disease characterized by low bone mass and microarchitectural deterioration of bone tissue, leading to enhanced bone fragility and a consequent increase in fracture risk. It is the most common human metabolic bone disorder. Established osteoporosis includes the presence of fractures.

Bone turnover occurs by the action of two major effector cell types within bone: the osteoclast, which is responsible for bone resorption, and the osteoblast, which synthesizes and mineralizes bone matrix. The actions of osteoclasts and osteoblasts are highly coordinated. Osteoclast precursors are recruited to the site of turnover; they differentiate and fuse to form mature osteoclasts which then resorb bone. Attached to the bone surface, osteoclasts produce an acidic microenvironment in a tightly defined junction between the specialized osteoclast border membrane and the bone matrix, thus allowing the localized solubilization of bone matrix. This in turn facilitate the proteolysis of demineralized bone collagen. Matrix degradation is thought to release matrix-associated growth factor and cytokines, which recruit osteoblasts in a temporally and spatially controlled fashion. Osteoblasts synthesize and secrete new bone matrix proteins, and subsequently mineralize this new matrix. In the normal skeleton this is a physiological process which does not result in a net change in bone mass. In pathological states, such as osteoporosis, the balance between resorption and formation is altered such that bone loss occurs. See WO 99/45923.

The osteoclast itself is the direct or indirect target of all currently available osteoporosis agents with the possible exception of fluoride. Antiresorptive therapy prevents further bone loss in treated individuals. Osteoblasts are derived from multipotent stem cells which reside in bone marrow and also gives rise to adipocytes, chondrocytes, fibroblasts and muscle cells. Selective enhancement of osteoblast activity is a highly desirable goal for osteoporosis therapy since it would result in an increase in bone mass, rather than a prevention of further bone loss. An effective anabolic therapy would be expected to lead to a significantly greater reduction in fracture risk than currently available treatments.

The agonists or antagonists to the newly discovered polypeptides may act as antiresorptive by directly altering the osteoclast differentiation, osteoclast adhesion to the bone matrix or osteoclast function of degrading the bone matrix. The agonists or antagonists could indirectly alter the osteoclast function by interfering in the synthesis and/or modification of effector molecules of osteoclast differentiation or function such as cytokines, peptide or steroid hormones, proteases, etc.

The agonists or antagonists to the newly discovered polypeptides may act as anabolics by directly enhancing the osteoblast differentiation and/or its bone matrix forming function. The agonists or antagonists could also indirectly alter the osteoblast function by enhancing the synthesis of growth factors, peptide or steroid hormones or decreasing the synthesis of inhibitory molecules.

In a further embodiment, human protein phosphatase IIC-like enzyme or a fragment or derivative thereof may be added to cells to stimulate cell proliferation. In particular, human protein phosphatase IIC-like enzyme may be added to a cell or cells in vivo using delivery mechanisms such as liposomes, viral based vectors, or electroinjection for the purpose of promoting regeneration or cell differentiation of the cell or cells. In addition, human protein phosphatase IIC-like enzyme may be added to a cell, cell line, tissue, or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for human protein phosphatase IIC-like enzyme may be administered to a cell to stimulate cell proliferation, as described above.

In another further embodiment, a vector capable of expressing human protein phosphatase IIC-like enzyme or a portion or a biologically active variant thereof, may be administered to a cell or cells in vivo using delivery mechanisms, or to a cell to stimulate cell proliferation, as described above.

Increased expression of human protein phosphatase IIC-like enzyme may be associated with increased cell proliferation. Therefore, in one embodiment, an antagonist of human protein phosphatase IIC-like enzyme or a portion or a biologically active variant thereof may be administered to a subject to prevent or treat cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Cancers which can be treated according to the invention include, but are not limited to, adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for human protein phosphatase IIC-like enzyme may be used directly as an antagonist, or indirectly as a targeting or delivery mechanism for bringing a pharmaceutical agent to cells or tissue which express human protein phosphatase IIC-like enzyme.

In still another embodiment, a vector expressing the complementary sequence or antisense of the polynucleotide encoding human protein phosphatase IIC-like enzyme or a portion or biologically active variant thereof may be administered to a subject to prevent or treat a disorder associated with cell proliferation including, but not limited to, the types of cancer listed above.

In a further embodiment, an antagonist of human protein phosphatase IIC-like enzyme or a portion or a biologically active variant thereof may be administered to a subject to prevent or treat inflammation of any type and, in particular, that which results from a particular disorder or conditions. Such disorders and conditions associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scieroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for human protein phosphatase IIC-ike enzyme may be used directly as an antagonist, or indirectly as a targeting or delivery mechanism for bringing a pharmaceutical agent to cells or tissue which express human protein phosphatase IIC-like enzyme.

In another further embodiment, a vector expressing the complementary sequence or antisense of the polynucleotide encoding human protein phosphatase IIC-like enzyme or a portion or a biologically active variant thereof may be administered to a subject to prevent or treat inflammation of any type including, but not limited to, those listed above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects protein phosphatase IIC-like enzyme activity can be administered to a human cell, either in vitro or in vivo, to reduce protein phosphatase IIC-like enzyme activity. The reagent preferably binds to an expression product of a human protein phosphatase IIC-like enzyme gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 mmol of liposome delivered to about $10^6$ cells, more preferably about 1.0 μg of DNA per 16 mmol of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 mmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Determination of a Therapeutically Effective Dose

The determination of a therapeutically effective dose is well within the capability of those skilled in the art. A therapeutically effective dose refers to that amount of active ingredient which increases or decreases extracellular matrix degradation relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LDs_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a protein phosphatase IIC-like enzyme polynucleotide or activity of a protein phosphatase IIC-like enzyme polypeptide by at least about 10, preferably about 50, more preferably about 75, 90, or 100% relative to the absence of the reagent. The effectiveness of the mechanism chosen to decrease the level of expression of a protein phosphatase IIC-like enzyme polynucleotide or the activity of a protein phosphatase IIC-like enzyme polypeptide can be assessed using methods well known in the art, such as hybridization of nucleotide probes to protein phosphatase IIC-like enzyme-specific mRNA, quantitative RT-PCR, immunologic detection of a protein phosphatase IIC-like enzyme polypeptide, or measurement of protein phosphatase IIC-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents, patent applications, and references cited in this disclosure are expressly incorporated herein by reference in their entireties. A more complete understanding can be obtained by reference to the following specific examples, which are provided for purposes of illustration only and are not intended to limit the scope of the invention.

EXAMPLE 1

Detection of Protein Phosphatase IIc-like Enzyme Activity

The polynucleotide of SEQ ID NO: 1 is inserted into the expression vector pCEV4 and the expression vector pCEV4-protein phosphatase IIC-like enzyme polypeptide obtained is transfected into human embryonic kidney 293 cells. Form these cells extracts are obtained and protein phosphatase IIC-like enzyme activity is determined against phosphohistone by the quantification of liberated $^{32}P$ from phosphohistone produced as described in Example 4 below according to previously established methods (see Honkanen et al., *J. Biol. Chem.* 265, 19401–04, 1990; Honkanen et al., *Mol. Pharmacol.* 40, 577–83, 1991; Critz & Honkanen, *Neuroprotocols* 6, 78–83, 1995). Assays (80 µl final volume) are conducted in 50 mM Tris-buffer (pH 7.4) containing 0.5 mM DTT, 4 mM EDTA, and phosphohiston (2 µM $PO_4$). The assay is initiated by the addition of the cell extract (30 µl) to a 1.5 ml microfuge tube containing 50 µl of dilute homogenate. Assays are conducted at 30° C. for 10 minutes and are stopped by the addition of 100 µl of 1N $H_2SO_4$ containing 1 mM $K_2PO_4$. $^{32}$P-Phosphate liberated by the cell extract is then extracted as a phosphomolybdate complex and measured according to the methods of Killilea et al., *Arch. Biochem. Biophys.* 191, 638–46, 1978). Briefly, free phosphate is extracted by adding 20 µl of ammonium molybdate (7.5% w/v in 1.4 N $H_2SO_4$) and 250 µl of isobutanol: benzene (1:1, v/v) to each tube. The tubes are mixed vigorously for approximately 10 seconds followed by centrifugation at 14,000×g for 2 minutes. Aliquots of the upper phase (100 µl) are removed for counting, and radioactivity is quantified with a scintillation counter. It is shown that the polypeptide of SEQ ID NO: 2 has a protein phosphatase IIC-like enzyme activity.

EXAMPLE 2

Expression of Recombinant Human Protein Phosphatase IIc-like Enzyme

The *Pichia pastoris* expression vector pPICZB (Invitrogen, San Diego, Calif.) is used to produce large quantities of a recombinant human protein phosphatase IIC-like enzyme in yeast. The encoding DNA sequence is derived from the nucleotide sequence shown in SEQ ID NO:1. Before insertion into vector pPICZB, the DNA sequence is modified by well known methods in such a way that it contains at its 5'-end an initiation codon and at its 3'-end an enterokinase cleavage site, a His6 reporter tag, and a termination codon. Moreover, at both termini recognition sequences for restriction endonucleases are added.

After digestion of the multiple cloning site of pPICZ B with the corresponding restriciton enzymes, the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks, and the recombinantly produced protein isolated from the culture by affinity chromatography (Ni-NTA-Resin) in the presence of 8 M urea The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human protein phosphatase IIC-like enzyme is obtained.

EXAMPLE 3

Identification of a Test Compound Which Binds to a Protein Phosphatase IIC-like Enzyme Polypeptide Purified protein phosphatase IIC-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. Protein phosphatase IIC-like enzyme polypeptides comprise the amino acid sequence shown in SEQ ID NO:2. The test compounds comprise a fluorescent tag. The samples are incubated for 5 minutes to one hour. Control samples are incubated in the absence of a test compound.

The buffer solution containing the test compounds is washed from the wells. Binding of a test compound to a protein phosphatase IIC-like enzyme polypeptide is detected by fluorescence measurements of the contents of the wells. A test compound which increases the fluorescence in a well by at least 15% relative to fluorescence of a well in which a test compound was not incubated is identified as a compound which binds to a protein phosphatase IIC-like enzyme polypeptide.

EXAMPLE 4

Measurement of Protein Phosphatase Activity and the Preparations of Phosphoprotein Substrates Phosphorylase kinase (EC 2.7.1.38), protein kinase A (3':5'-cyclic AMP dependent) phosphorylase b (EC 2.4.1.1), and crude histone (type 2AS) are obtained from Sigma Chemical Co. Okadaic acid can be obtained from a variety of commercial sources.

Phosphohistone with a specific activity >4.5×10$^6$ dpm/nmol incorporated phosphate is prepared by the phosphorylation of bovine brain histone (type 2AS from Sigma Chem. Co) with 3':5'-cAMP-dependent protein kinase (from rabbit muscle) in the presence of $\gamma^{32}$P-ATP essentially as described by Honkanen et al. (*J. Biol. Chem.* 265, 19401–04 (1990) and *Mol. Pharmacol.* 40, 577–83 (1991). The reaction is started by the addition of protein kinase A (1 mg) to a 20 mM Tris-buffer (pH 6.2) containing 20 mg of histone, 1 mCi $\gamma^{32}$ P-ATP (150 µM ATP), 100 µM cAMP, 5 mM DTT, and 5 mM $MgCl_2$. The final volume is 4 ml, and the phosphorylation reaction is allowed to continue for 3.5 hours at 30° C.

The reaction is terminated by the addition of 1.3 ml of ice cold 100% trichloroacetic acid. After placing the tube in ice for 10 minutes, the precipitated phosphohistone is collected by centrifugation at 3000×g for 5 minutes. The supernatant is discarded, and the pellet is redissolved in 4 ml of 0.8 M Tris-Cl (pH 8.5). Trichloroacetic acid (1.3 ml of 100% w/v) is added to precipitate the phosphohistone a second time, and the precipitation-resuspension washing procedure is repeated 5 times.

The pellet produced after the final trichloroacetic acid precipitation is washed 2 times with 4 ml of ethanol:ethyl ether (1:4; v/v) and then 2 additional times with 4 ml acidified ethanol:ethyl ether (1:4; 0.1 N HCl). The washed phoshohistone pellet is allowed to air dry and resuspended in 5 mM Tris HCl (pH 7.4).

Phosphorylase a is prepared essentially according to the methods described in Honkanen et al., *Mol. Pharmacol* 40, 577–83 (1991). Briefly, $^{32}$ P-phosphorylase a is prepared by the phosphorylation of phosphorylase β with phosphorylase kinase using 30 mg of phosphorylase b, 1.4 mCi of $\gamma^{32}$P-ATP (to give 1×10$^4$ cpm pmole$^{-1}$) and 100 U of phosphorylase kinase. The phosphorylation reaction is carried out for 1.5 hour at pH 8.2 and 30° C. After termination of the reaction, phosphorylase a is crystallized by adjustment of the pH to 6.8 and placing the mixture on ice. The crystals are collected by centrifugation and washed extensively with 20 mM Tris-HCL, 50 mM 2-mercaptoethanol, pH 6.8.

After washing, the crystals are dissolved by the addition of NaCl to achieve a final concentration of 100 mM. The solution is dialyzed overnight at 4° C. against 20 mM Tris-HCL, 50 mM 2-mercaptoethanol, pH 6.8. (2×4 liters). The phosphorylase a, which recrystalizes during dialysis, is redissolved in assay buffer containing 100 mM NaCl for immediate use or 100% glycerol for short term storage. This results in phosphorylase a with a specific activity of approximately 6×10$^6$ cpm/nmol of incorporated phosphate.

Determination of protein phosphatase activity. Protein phosphatase activity against phosphohistone is determined by the quantification of liberated $^{32}$P from phosphohistone according to previously established methods (see Honkanen et al., *J. Biol. Chem.* 265, 19401–04, 1990; Honkanen et al., *Mol. Pharmacol.* 40, 577–83, 1991; Critz & Honkanen, Neuroprotocols 6, 78–83, 1995). Assays (80 µl final volume) are conducted in 50 mM Tris-buffer (pH 7.4) containing 0.5 mM DTT, 4 mM EDTA, and phosphoprotein (2 µM PO$_4$). The assay is initiated by the addition of substrate (30 µl) to a 1.5 ml microfuge tube containing 50 µl of dilute homogenate. Assays are conducted at 30° C. for 10 minutes and are stopped by the addition of 100 µl of 1N H$_2$SO$_4$ containing 1 mM K$_2$HPO$_4$.

$^{32}$P-Phosphate liberated by the enzyme is then extracted as a phosphomolybdate complex and measured according to the methods of Killilea et al., *Arch. Biochem. Biophys.* 191, 638–46, 1978). Briefly, free phosphate is extracted by adding 20 µl of ammonium molybdate (7.5% w/v in 1.4 N H$_2$SO$_4$) and 250 µl of isobutanol:benzene (1:1, v/v) to each tube. The tubes are mixed vigorously for approximately 10 seconds followed by centrifugation at 14,000×g for 2 minutes. Aliquots of the upper phase (100 µl) are removed for counting, and radioactivity is quantified with a scintillation counter.

For inhibition studies, fostriecin or okadaic acid or a test compound is added to the enzyme mixture 10 minutes before the reaction is initiated with the addition of substrate. Controls receive solvent alone, and in all experiments the amount of enzyme is diluted to ensure that the samples are below the titration endpoint. The titration endpoint is defined as the concentration of enzyme after which further dilution no longer affects the IC$_{50}$ of the toxin, and represents a point where the concentration of enzyme used in the assay no longer approaches that of the toxin. This ensures that IC$_{50}$ represents the potency of the inhibitor alone and is not representative of a combination of potency of the toxin and titration artifacts of the assay system. Preliminary assays are performed to ensure the dephosphorylation reaction is linear with respect to enzyme concentration and time.

EXAMPLE 5

Identification of a Test Compound which Decreases Protein Phosphatase IIC-like Enzyme Activity Cellular extracts from cells comprising human protein phosphatase IIC-like enzyme are contacted with test compounds from a small molecule library and assayed for protein phosphatase IIC-like enzyme activity. Control extracts, in the absence of a test compound, also are assayed. Human protein phosphatase IIC-like enzyme activity can be measured, for example, as described in Example 3, above.

A test compound which decreases protein phosphatase IIC-like enzyme activity of the extract relative to the control extract by at least 20% is identified as a protein phosphatase IIC-like enzyme inhibitor.

EXAMPLE 6

Identification of a Test Compound which Decreases Protein Phosphatase IIc-like Enzyme Gene Expression A test compound is administered to a culture of the breast tumor cell line MDA-468 and incubated at 37° C. for 10 to 45 minutes. A culture of the same type of cells incubated for the same time without the test compound provides a negative control.

RNA is isolated from the two cultures as described in Chirgwin et al., *Biochem.* 18, 5294–99, 1979). Northern blots are prepared using 20 to 30 µg total RNA and hybridized with a $^{32}$P-labeled protein phosphatase IIC-like enzyme-specific probe at 65° C. in Express-hyb (CLONTECH). The probe comprises at least 11 contiguous nucleotides selected from the complement of SEQ ID NO:1. A test compound which decreases the protein phosphatase IIC-like enzyme-specific signal relative to the signal obtained in the absence of the test compound is identified as an inhibitor of protein phosphatase IIC-like enzyme gene expression.

EXAMPLE 7

Inhibition of Apoptosis by Inhibiting Human Protein Phosphatase IIC-like Enzyme with Antisense Oligonucleotides The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% CO$_2$ atmosphere.

Phosphorothioate oligoribonucleotides are synthesized on an Applied Biosystems Model 380B DNA synthesizer using phosphoroamidite chemistry. The test oligonucleotide is a sequence of 24 bases: 5'-TAC-CGG-AGT-GCC-GAG-GACGTA-GCG-3' (complementary to the nucleotides at positions 1–24 of SEQ ID NO:1). As a control, another (random) sequence 5'-TCA-ACT-GAC-TAG-ATG-TAC-ATGGAC-3' is used. Following assembly and deprotection, oligonucleotides are ethanol-precipitated twice, dried, and suspended in phosphate buffered saline at the desired concentration. Purity of these oligonucleotides is tested by capillary gel electrophoresis and ion exchange HPLC. The purified oligonucleotides are added to the culture medium at a concentration of 10 µM.

The addition of the test oligonucleotide for seven days results in significantly reduced expression of the phosphatase IIC as determined by Western blotting. This effect is not observed with the control oligonucleotide. After 3 to 7 days, the number of cells is counted using an automatic cell counter. The microscopic appearance of cells in cultures treated with the control oligonucleotide is compared with the microscopic appearance of cells in cultures treated with the test oligonucleotide. Nuclei of cells in the test dishes are largely intact, whereas in the control dishes, changes in morphology characteristic of apoptosis has occurred, indicating that inhibition of human protein phosphatase IIC prevents apoptosis.

EXAMPLE 8

Treatment of Breast Cancer with a Reagent which Specifically Binds to a Protein Phosphatase IIC-like Enzyme Gene Product Synthesis of antisense protein phosphatase IIC-like enzyme oligonucleotides comprising at least 11 contiguous nucleotides selected from the complement of SEQ ID NO:1 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the *Limulus* Amebocyte Assay (Bang, *Biol. Bull.* (Woods Hole, Mass.) 105, 361–362, 1953).

An aqueous composition containing the antisense oligonucleotides at a concentration of 0.1–100 μM is administered directly to a patient's breast tumor by injection. The size of the tumor is thereby decreased.

EXAMPLE 9

Tissue-specific Expression of Protein Phosphatase IIC-like Gene

As a first step to establishing a role for protein phosphatase IIC-like enzyme in the pathogenesis of COPD, expression profiling of the gene was done using real-time quantitative PCR (TaqMan) with RNA samples isolated from a wide range of human cells and tissues. Total RNA samples were either purchased from commercial suppliers or purified in-house. Two panels of RNAs were used for profiling: a whole body organ panel (Table 1) and a respiratory specific panel (Table 2).

Real-tine quantitative PCR. This technique is a development of the kinetic analysis of PCR first described by Higuchi et al. (*BioTechnology* 10, 413–17, 1992; *BioTechnology* 11, 1026–30, 1993). The principle is that at any given cycle within the exponential phase of PCR, the amount of product is proportional to the initial number of template copies. PCR amplification is performed in the presence of an oligonucleotide probe (TaqMan probe) that is complementary to the target sequence and labeled with a fluorescent reporter dye and a quencher dye. During the extension phase of PCR, the probe is cleaved by the 5'–3' endonuclease activity of Taq DNA polymerase, releasing the fluorophore from the effect of the quenching dye (Holland et al., *Proc. Natl. Acad. Sci. U.S.A.* 88, 7276–80, 1991). Because the fluorescence emission increases in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

RNA extraction and cDNA preparation. Total RNA from each of the 'in-house' samples listed in Table 2 was isolated using Qiagen's (Crawley, West Sussex, UK) RNeasy system according to the manufacturer's protocol. The concentration of purified RNA was determined using RiboGreen RNA quantitation kit (Molecular Probes Europe, The Netherlands). RNA concentrations of the samples purchased from commercial suppliers were also determined using RiboGreen. For the preparation of cDNA, 1 μg of total RNA was reverse transcribed using 200U of SUPERSCRIPT™ II RNaseH⁻Reverse Transcriptase (Life Technologies, Paisley, UK), 10 mM dithiothreitol, 0.5 mM of each dNTP, and 5 μM random hexamers (PE Applied Biosystems, Warrington, Cheshire, UK) in a final volume of 20 μl according to the manufacturer's protocol.

TaqMan quantitative analysis. Specific primers and probe were designed according to the recommendations of PE Applied Biosystems and are listed below:

```
Forward primer:
5'-TCAGTTCCTCTTTCCCGATCTG-3'

Reverse primer:
5'-CCTAAAACCATCCAGCGAAAGTT-3'

Probe:
5'-(FAM)-TGCTGCCTTAACAATGAGGAAGCTCTCCA-3'
``` where FAM=6-carboxy-fluorescein.

Quantitative PCR was performed with long of reverse transcribed RNA from each sample. Each determination was done in duplicate.

The assay reaction mix was as follows: 1× X final TaqMan Universal PCR Master Mix (from 2× stock) (PE Applied Biosystems, CA); 900 nM forward primer; 900 nM reverse primer; 200 nM probe; 10 ng cDNA; and water to 25μl.

Each of the following steps were carried out once: pre PCR, 2 minutes at 50° C., and 10 minutes at 95° C. The following steps are carried out 40 times: denaturation, 15 seconds at 95° C., annealing/extension, 1 minute at 60° C.

Real-time quantitative PCR was done using an ABI Prism 7700 Sequence Detector. The $C_T$ value generated for each reaction was used to determine the initial template concentration (copy number) by interpolation from a universal standard curve. The level of expression of the target gene in each sample was calculated relative to the sample with the lowest expression of the gene.

The relative expression of protein phosphatase IIC-like gene across various human tissues is shown in FIG. 16. The gene was ubiquitously expressed, with liver exhibiting the lowest level of expression and testis the highest. Expression of the gene in lung was investigated further by profiling its expression in some of the constituent cell types of this tissue. In these samples, abundant expression was detected in trachea and whole lung tissue but in all of the other cells types tested the gene was either expressed at a very low level or not at all (FIG. 17).

TABLE 1

Human organ RNA panel used for real-time quantitative PCR.

| Tissue | Cat. # |
|---|---|
| Adrenal gland | Human Panel V, K4004-1 |
| Bone marrow | Human Panel II, K4001-1 |
| Brain | Human Panel I, K4000-1 |
| Colon | Human Panel II, K4001-1 |
| Heart | Human Panel III, K4002-1 |
| Kidney | Human Panel I, K4000-1 |
| Liver | Human Panel I, K4000-1 |
| Lung | Human Panel I, K4000-1 |
| Mammary gland | Human Panel III, K4002-1 |
| Pancreas | Human Panel V, K4004-1 |
| Prostate | Human Panel III, K4002-1 |
| Salivary gland | Human Panel V, K4004-1 |
| Skeletal muscle | Human Panel III, K4002-1 |
| Small intestine | Human Panel II, K4001-1 |
| Spleen | Human Panel II, K4001-1 |
| Stomach | Human Panel II, K4001-1 |
| Testis | Human Panel III, K4002-1 |
| Thymus | Human Panel II, K4001-1 |
| Thyroid | Human Panel V, K4004-1 |
| Uterus | Human Panel III, K4002-1 |

All samples were obtained from Clontech UK Ltd, Basingstoke, UK.

TABLE 2

Human respiratory specific RNA panel used for real-time quantitative PCR.

| Tissue/cell type | Supplier, cat # |
| --- | --- |
| Lung (fetal) | Takara (Japan) |
| Lung | Clontech, Human Panel I, K4000-1 |
| Trachea | Clontech, Human Panel I, K4000-1 |
| Cultured human bronchial epithelial cells | In-house |
| Cultured airway smooth muscle cells | In-house |
| Cultured small airway epithelial cells | In-house |
| Primary cultured alveolar type II cells | In-house |
| Cultured H441 cells (Clara-like) | In-house |
| Freshly isolated polymorphonuclear leukocytes (neutrophils) | In-house |
| Freshly isolated monocytes | In-house |
| Cultured monocytes (macrophage-like) | In-house |

The invention claimed is:

1. A method of screening for candidate therapeutic agents, comprising the steps of:
   contacting a protein comprising the amino acid sequence shown in SEQ ID NO:2 with a test compound;
   assaying for binding between the protein and the test compound; and
   identifying a test compound that binds to the protein as a candidate therapeutic agent that may be useful for treating a disorder selected from the group consisting of a disorder associated with an increase in apoptosis and a disease associated with a decrease in apoptosis.

2. The method of claim 1 wherein either the test compound or the protein comprises a detectable label.

3. The method of claim 1 wherein either the test compound or the protein is bound to a solid support.

* * * * *